(12) United States Patent
Coelho et al.

(10) Patent No.: US 9,487,471 B1
(45) Date of Patent: Nov. 8, 2016

(54) SYNTHESIS OF PYRETHROIDS AND PYRETHROID-CONTAINING COMPOSITIONS

(71) Applicant: PROVIVI, INC., Santa Monica, CA (US)

(72) Inventors: Pedro Coelho, Santa Monica, CA (US); Peter Meinhold, Topanga, CA (US); Mike M. Y. Chen, Pasadena, CA (US)

(73) Assignee: PROVIVI, INC., Santa Monica, CA (US)

( * ) Notice: Subject to any disclaimer, the term of this patent is extended or adjusted under 35 U.S.C. 154(b) by 0 days.

(21) Appl. No.: 14/686,647

(22) Filed: Apr. 14, 2015

Related U.S. Application Data

(60) Provisional application No. 61/979,449, filed on Apr. 14, 2014.

(51) Int. Cl.
*C07C 69/747* (2006.01)
*A01N 53/00* (2006.01)

(52) U.S. Cl.
CPC ............. *C07C 69/747* (2013.01); *A01N 53/00* (2013.01); *C07C 2101/02* (2013.01); *C07C 2101/10* (2013.01)

(58) Field of Classification Search
None
See application file for complete search history.

(56) References Cited

U.S. PATENT DOCUMENTS

2016/0039737 A1    2/2016  Champagne et al.

FOREIGN PATENT DOCUMENTS

IN    WO 2011/095991    *  8/2011   ............. C07C 62/32

OTHER PUBLICATIONS

Higman, C.M et al; Olefin Metathesis at the Dawn of Implementation in Pharmaceutical and Specialty-Chemicals Manufacturing; Angew. Chem. Int. Ed. (2016) 55, 3552-3565.

* cited by examiner

*Primary Examiner* — Samantha Shterengarts
(74) *Attorney, Agent, or Firm* — Kilpatrick Townsend & Stockton LLP

(57) ABSTRACT

The present invention provides methods for synthesizing pyrethroid compounds. The methods include forming a first reaction comprising an olefin and an allethrolone-type unsaturated alcohol under conditions sufficient to form a metathesis product and converting the metathesis product to the pyrethroid. Methods of the invention can be used to prepare compounds including pyrethrin I, cinerin I, jasmolin I, pyrethrin II, cinerin II, and jasmolin II as well as other synthetic pyrethroid compounds. Insecticidal compositions and methods for controlling insects are also described.

17 Claims, 11 Drawing Sheets

R = H, Me, Ac, i-Pr, chrysanthemate, pyrethrate

SYNTHESIS OF PYRETHROIDS AND PYRETHROID-CONTAINING COMPOSITIONS

CROSS-REFERENCES TO RELATED APPLICATIONS

The present application claims priority to U.S. Provisional Patent Application No. 61/979,449, filed on Apr. 14, 2014, which application is incorporated herein by reference in its entirety.

BACKGROUND OF THE INVENTION

Pyrethrum is a natural insecticide currently extracted from *chrysanthemum* flowers (genus *Chrysanthemus*, e.g., *C. cinerariifolium* and *C. coccineum*). These extracts have been used as insecticides for a long time. The insecticidal neurotoxic activity of pyrethrum is based on the individual components: three naturally occurring, closely related insecticidal esters of chrysanthemic acid (pyrethrins I) and three closely related esters of pyrethric acid (pyrethrins II). As used herein, all 6 esters may be collectively referred to as pyrethrins or pyrethrum.

Pyrethrum extracted from flowers is expensive and supply is oftentimes limited and not reliable. Furthermore, the ratio of the six insecticidal components of pyrethrum is determined by biosynthesis and cannot be altered. The present invention provide new methods for preparing pyrethrins and related compounds, addressing the limitations associated with pyrethrum extract obtained via known processes.

BRIEF SUMMARY OF THE INVENTION

In one aspect, the invention provides a method of synthesizing a pyrethroid of Formula I:

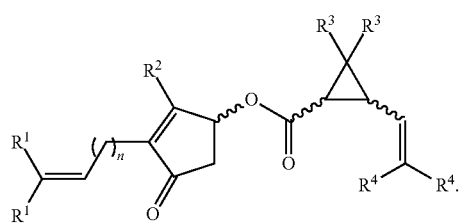

The method includes:

a) forming a first reaction mixture comprising an olefin of Formula II:

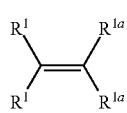

and an alcohol of Formula III:

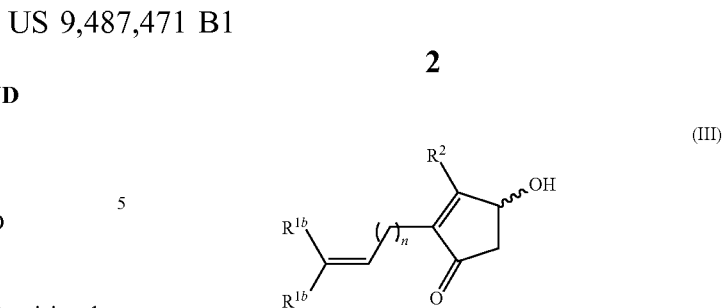

under conditions sufficient to form a metathesis product of Formula IV:

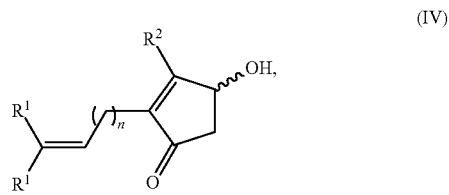

and b) converting the metathesis product to the pyrethroid;

wherein:

each $R^1$ and $R^2$ is independently selected from H, halo, $C_{1-12}$ alkyl, $C_{1-12}$ haloalkyl, $C_{1-12}$ alkoxy, $C_{1-12}$ alkenyl, $C_{1-12}$ haloalkenyl, $C_{1-12}$ alkenyloxy, and 3- to 6-membered heterocyclyl, wherein each alkyl, haloalkyl, alkoxy, alkenyl, haloalkenyl, and alkenyloxy group is optionally substituted with 1-5 substituents independently selected from hydroxy, $C_{1-6}$ alkoxy, and cyano;

each $R^{1a}$ and $R^{1b}$ is independently selected from H; halo; $C_{1-6}$ alkyl; $C_{1-6}$ haloalkyl; and —O—SO$_2$R$^c$, where $R^c$ is selected from $C_{1-6}$ alkyl, $C_{1-6}$ haloalkyl, and $C_{6-10}$ aryl;

each $R^3$ and $R^4$ is independently selected from H; $C_{1-18}$ alkyl; $C_{2-18}$ alkenyl; $C_{2-18}$ alkynyl; $C_{6-10}$ aryl optionally substituted with one or more $R^8$ groups; $C_1$-$C_6$ alkoxy optionally substituted with one or more $R^8$ groups; halo; hydroxy; cyano; C(O)N(R$^5$)$_2$; NR$^5$C(O)R$^6$; C(O)R$^6$; C(O)OR$^6$; and N(R$^7$)$_2$;

each $R^5$ and $R^6$ is independently selected from H; $C_{1-12}$ alkyl optionally substituted with one or more $R^8$ groups; $C_{2-12}$ alkenyl optionally substituted with one or more $R^8$ groups; and $C_{6-10}$ aryl optionally substituted with one or more $R^8$ groups;

each $R^7$ is independently selected from H; $C_{6-10}$ aryl optionally substituted with one or more $R^8$ groups; and 6- to 10-membered heteroaryl optionally substituted with one or more $R^8$ groups; or two $R^7$ moieties, together with the nitrogen atom to which they are attached, form 6- to 18-membered heterocyclyl;

each $R^8$ is independently selected from halo, hydroxy, amino, alkylamino, alkoxy, haloalkyl, carboxy, amido, nitro, oxo, and cyano; and the subscript n is 0 or 1.

In some embodiments, converting the metathesis product to the pyrethroid comprises forming a second reaction mixture comprising the metathesis product and an esterification agent of Formula V:

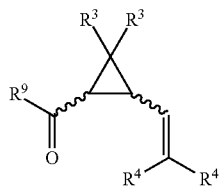

under conditions sufficient to form the pyrethroid, wherein $R^9$ is selected from halogen and —$OR^{9a}$, and $R^{9a}$ is selected from H, $C_{1-6}$ acyl, N-succinimidyl, and pentafluorophenyl.

In some embodiments, one $R^1$ is H and the other $R^1$ is selected from $C_{1-6}$ alkyl and $C_{1-6}$ alkenyl; one $R^{1a}$ is H and the other $R^{1a}$ is selected from H, $C_{1-6}$ alkyl, and $C_{1-6}$ haloalkyl; one $R^{1b}$ is H and the other $R^{1b}$ is selected from H, $C_{1-6}$ alkyl, and $C_{1-6}$ haloalkyl; $R^2$ and each $R^3$ are $C_{1-6}$ alkyl; one $R^4$ is $C_{1-6}$ alkyl and the other $R^4$ is selected from $C_{1-6}$ alkyl and $C(O)OR^6$, wherein $R^6$ is $C_{1-6}$ alkyl; and subscript n is 1.

In certain embodiments, the present invention provides synthesis routes to each of the six components of pyrethrum which can be mixed to provide a composition of the six components at the same ratio that is found in pyrethrum extracted from *chrysanthemum* flowers. In some embodiments, the present invention provides formulations of the composition of the six components at the same ratio that is found in pyrethrum extracted from *chrysanthemum* flowers. In some embodiments, mixtures of the six components of pyrethrum are mixed in ratios not found in *chrysanthemum* flowers. These mixtures can provide improved performance over natural pyrethrum.

In another aspect of the invention, pyrethrum is used as an insecticide in various formulations. The present invention is advantageous because pyrethrum has never been produced synthetically, at least not in commercial quantities.

Other objects, features, and advantages of the present invention will be apparent to one of skill in the art from the following detailed description and figures.

DETAILED DESCRIPTION OF THE INVENTION

I. Definitions

Figure 1:
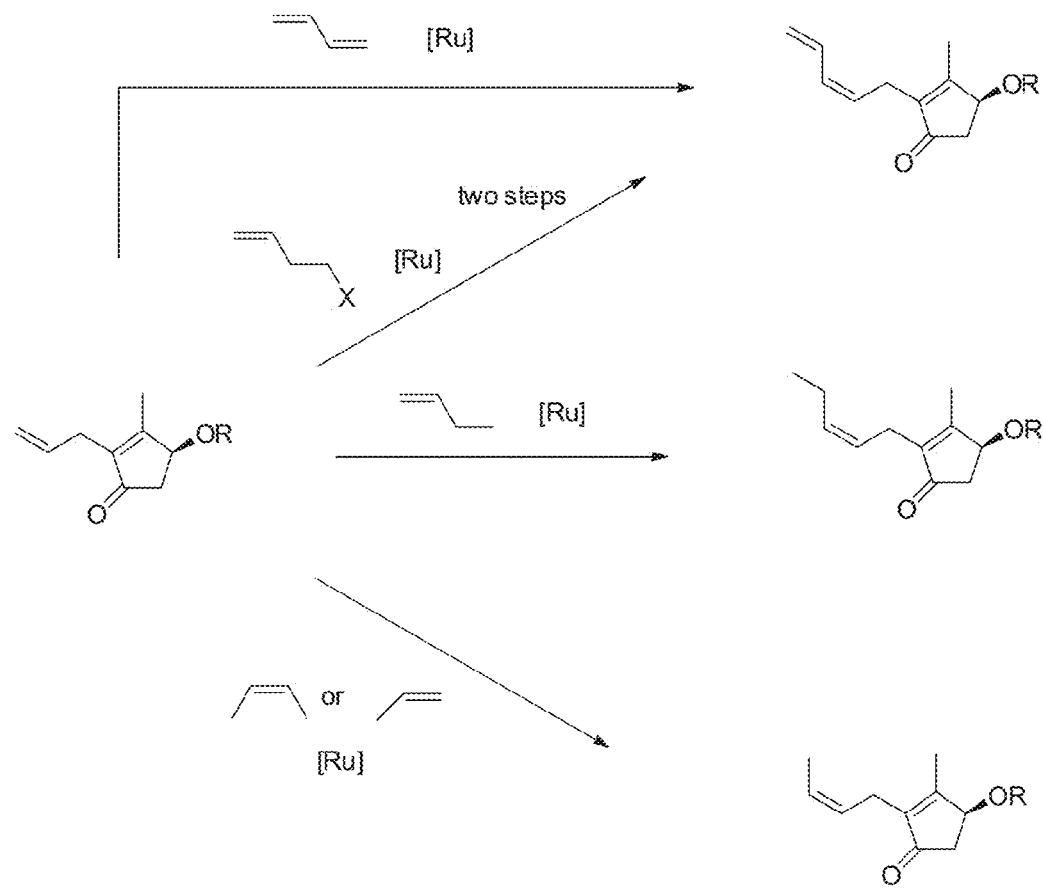
FIG. 1 shows a general scheme for making the alcohols in pyrethrum from protected allethrolones.

The following definitions and abbreviations are to be used for the interpretation of the invention. The term "invention" or "present invention" as used herein is a non-limiting term and is not intended to refer to any single embodiment but encompasses all possible embodiments.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the term "pyrethroid" refers to esters of chrysanthemic acid and structurally similar compounds. Naturally occurring pyrethroids, also referred to as "pyrethrins," include pyrethrin I, cinerin I, jasmolin I, pyrethrin II, cinerin II, and jasmolin II as described herein. Synthetic pyrethroids include, but are not limited to, permethrin, cyphenothrin, cypermethrin, flumethrin, and the like.

As used herein, the term "metathesis reaction" refers to a catalytic reaction which involves the interchange of alkylidene units (i.e., $R_2C=$ units) among compounds containing one or more carbon-carbon double bonds (e.g., olefinic compounds) via the formation and cleavage of the carbon-carbon double bonds. Metathesis can occur between two like molecules (often referred to as self-metathesis) and/or between two different molecules (often referred to as cross-metathesis).

As used herein, the term "metathesis catalyst" refers to any catalyst or catalyst system that catalyzes a metathesis reaction. One of skill in the art will appreciate that a metathesis catalyst can participates in a metathesis reaction so as to increase the rate of the reaction, but is itself not consumed in the reaction.

As used herein, the term "metathesis product" refers to an olefin containing at least one double bond, the bond being formed via a metathesis reaction.

As used herein, the term "olefin," also called an alkene, refers to a compound having at least one carbon-carbon double bond.

As used herein, the term "alcohol" refers to a compound having the formula $R_2C$—OH, wherein each R is independently selected from a hydrogen atom or a substituted carbon atom.

As used herein, the terms "halo" and "halogen" refer to fluorine, chlorine, bromine and iodine.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be optionally substituted with one or more moieties selected from halo, hydroxy, amino, alkylamino, alkoxy, haloalkyl, carboxy, amido, nitro, oxo, and cyano.

As used herein, the term "haloalkyl" refers to an alkyl moiety as defined above substituted with at least one halogen atom.

As used herein, the term "alkoxy" refers to an alkyl group having an oxygen atom that connects the alkyl group to the point of attachment: i.e., alkyl-O—. As for alkyl groups, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be optionally substituted with one or more moieties selected from halo, hydroxy, amino, alkylamino, alkoxy, haloalkyl, carboxy, amido, nitro, oxo, and cyano. "Alkenyloxy" refers to an alkenyl group having an oxygen atom that connects the alkyl group to the point of attachment: i.e., alkenyl-O—.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be optionally substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, and 1,3,5-hexatriynyl. Alkynyl groups can be optionally substituted with one or more moieties selected from halo, hydroxy, amino, alkylamino, alkoxy, haloalkyl, carboxy, amido, nitro, oxo, and cyano.

The term hydroxy refers to the moiety —OH.

The term "cyano" refers to a carbon atom triple-bonded to a nitrogen atom (i.e., the moiety —C≡N).

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be optionally substituted with one or more moieties selected from halo, hydroxy, amino, alkylamino, alkoxy, haloalkyl, carboxy, amido, nitro, oxo, and cyano.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. Heteroaryl groups can be optionally substituted with one or more moieties selected from halo, hydroxy, amino, alkylamino, alkoxy, haloalkyl, carboxy, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, and dithiane. Heterocyclyl groups can be optionally substituted with one or more le;.5qmoieties selected from halo, hydroxy, amino, alkylamino, alkoxy, haloalkyl, carboxy, amido, nitro, oxo, and cyano.

As used herein, the term "amino" refers to a moiety —NR$_3$, wherein each R group is H or alkyl. An amino moiety can be ionized to form the corresponding ammonium cation.

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)NR$_2$, wherein each R group is H or alkyl.

The term "nitro" refers to the moiety —NO$_2$.

As used herein, the term "oxo" refers to an oxygen atom that is double-bonded to a compound (i.e., O=).

As used herein, the term "dehydrohalogenation" refers to an organic reaction in which an alkyl halide is converted to the corresponding alkene when allowed to react with a base such as an alcoholic alkali. Dehydrohalogenation is commonly understood to occur via a β-elimination reaction; the base abstracts a proton from the β-carbon of the alkyl halide, and hydrogen halide is released as a result of the proton removal and the loss of the halide leaving group. An alkene is formed due to formation of a double bond between the α- and β-carbon.

The term "base" refers to a substance that is capable of accepting a proton (i.e., a hydrogen cation) to form a conjugate acid of the base. Examples of bases include, but are not limited to, Huenig's base (i.e., diisopropylethylamine), lutidines including 2,6-lutidine (i.e., 2,6-dimethylpyridine), triethylamine, pyridine, lithium diisopropylamide, bis (trimethylsilyl)amides, and t-butoxides.

The term "acid" refers to refers to Brønsted acids and Lewis acids. A Brønsted acid is a compound capable of donating a proton (i.e., H$^+$) to a Brønsted base. A Lewis acid is a compound that is capable of accepting electrons from an electron-donating Lewis base and forming a Lewis adduct by sharing the electrons donated by the Lewis base. Examples of acids include, but are not limited to, hydrochloric acid (HCl), acetic acid (CH$_3$COOH), and sulfamic acid (NH$_2$SO$_3$H).

As used herein, the term "forming a reaction mixture" refers to the process of bringing into contact at least two distinct species such that they mix together and can react, either modifying one of the initial reactants or forming a third distinct species, i.e., a product. It should be appreciated, however, that the resulting reaction product can be produced directly from a reaction between the added reagents or from an intermediate from one or more of the added reagents which can be produced in the reaction mixture.

The term "insecticidal composition" refers to a molecule or combination of molecules that controls, repels, inhibits or kills insects. The term includes ovicides and larvicides used against the eggs and larvae of insects, respectively.

The term "controlling insects" refers to killing insects, eradicating insects, arresting or inhibiting insect growth, reducing insect numbers, repelling insects, and/or imparting sterility to insects. The term "effective amount" refers to an amount of a pyrethroid compound—or a composition containing a pyrethroid compound—that results in the killing or eradication of insects, the arrest or inhibition of insect growth, the reduction of insect numbers, the repelling of insects, and/or the sterilization of insects. The term "insectically-effective amount" refers to an amount of a pyrethroid compound—or a composition containing a pyrethroid compound—that results in killing of insects.

II. Methods for Synthesizing Pyrethroids

The term "pyrethrum" (CAS NO. 8003-34-7) is defined as a mixture of the three naturally-occurring, closely-related insecticidal esters of chrysanthemic acid, Pyrethrins I (pyrethrin I, cinerin I and jasmolin I), and the three corresponding esters of pyrethric acid, Pyrethrins II (pyrethrin II, cinerin II and jasmolin II). The term "pyrethrin" is used herein to refer to a single compound selected from the group consisting of pyrethrin I, pyrethrin II, cinerin I, cinerin II, jasmolin I, and jasmolin II. The pyrethrins in any given natural pyrethrum extract vary in amount, depending on factors such as the plant variety, where it is grown, and the time of harvest.

Naturally-occurring pyrethrins share the general structural Formula 1:

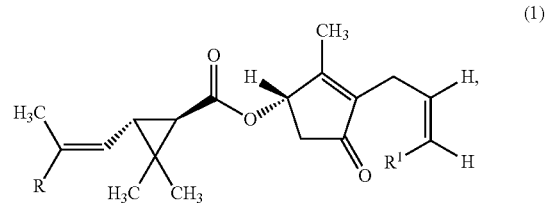

wherein R is —CH$_3$ for chrysanthemates or —CO$_2$CH$_3$ for pyrethrates; and R$_1$ is —CH=CH$_2$ for pyrethrin, —CH$_3$ for cinerin, or —CH$_2$CH$_3$ for jasmolin.

Pyrethrin I (CAS No. 121-21-1) is also known as (Z)—(S)-2-methyl-4-oxo-3-(penta-2,4-dienyl)cyclopent-2-enyl (1R)-trans-2,2-dimethyl-3-(2-methylprop-1-enyl)cyclopropanecarboxylate, having the structure:

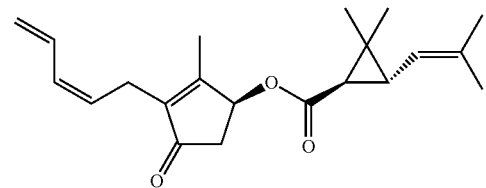

Cinerin I (CAS No. 25402-06-6) is also known as (Z)—(S)-3-(but-2-enyl)-2-methyl-4-oxocyclopent-2-enyl(1R)-trans-2,2-dimethyl-3-(2-methylprop-1-enyl)cyclopropanecarboxylate, having the structure:

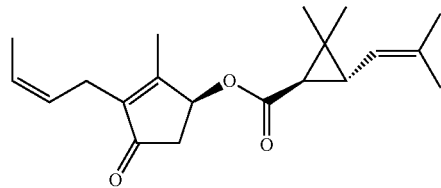

Jasmolin I (CAS No. 4466-14-2) is also known as (Z)—(S)-2-methyl-4-oxo-3-(pent-2-enyl)cyclopent-2-enyl(1R)-trans-2,2-dimethyl-3-(2-methylprop-1-enyl)cyclopropanecarboxylate, having the structure:

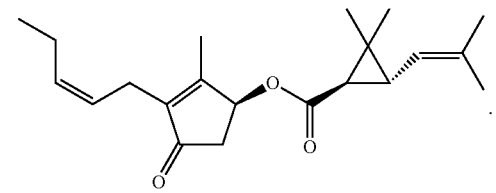 [SMILES: CC/C=C\CC1=C(C)[C@@H](OC(=O)[C@@H]2[C@@H](C=C(C)C)C2(C)C)CC1=O]

Pyrethrin II (CAS No. 121-29-9) is also known as (Z)—(S)-2-methyl-4-oxo-3-(penta-2,4-dienyl)cyclopent-2-enyl (E)-(1R)-trans-3-(2-methoxycarbonylprop-1-enyl)-2,2-dimethyl-cyclopropanecarboxylate, having the structure:

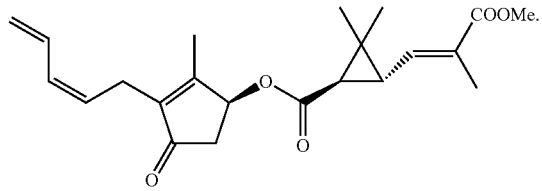 [SMILES: C=C/C=C\CC1=C(C)[C@@H](OC(=O)[C@@H]2[C@@H](/C=C(\C)C(=O)OC)C2(C)C)CC1=O]

Cinerin II (CAS No. 121-20-0) is also known as (Z)—(S)-3-(but-2-enyl)-2-methyl-4-oxocyclopent-2-enyl(E)-(1R)-trans-3-(2-methoxycarbonylprop-1-enyl)-2,2-dimethyl-cyclopropanecarboxylate, having the structure:

Jasmolin II (CAS No. 1172-63-0) is also known as (Z)—(S)-2-methyl-4-oxo-3-(pent-2-enyl)cyclopent-2-enyl (E)-(1R)-trans-3-(2-methoxycarbonylprop-1-enyl)-2,2-dimethyl-cyclopropanecarboxylate, having the structure:

A number of pyrethroids can be prepared according to the methods of the invention. In general, pyrethroids are characterized by an ester core having a structure according to Formula 2:

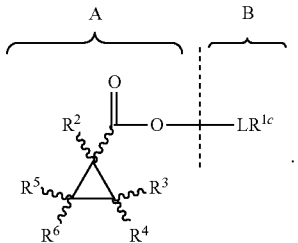

(2)

Formula 2 is presented above as a cyclopropyl carboxylate moiety ("A") esterified with an $LR^{1c}$ moiety ("B"), with $R^{1c}$ defined as for $R^C$. The methods of the invention can be used to prepare pyrethroids and pyrethroid intermediates having a variety of "A" moieties connected to any of a variety of "B" moieties. For example, the pyrethroids can have an "A" moiety selected from:

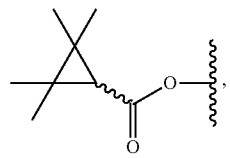

A1

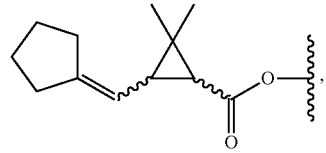

A2

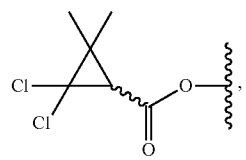

A3

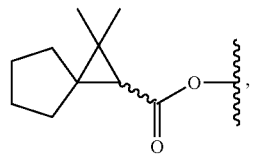

A4

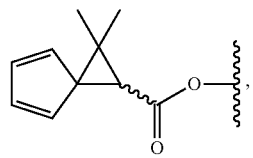

A5

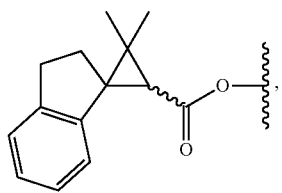

A6

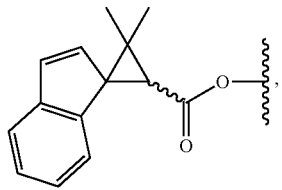

A7

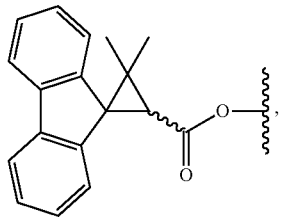

A8

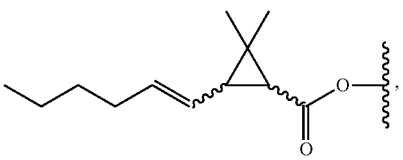

A9

-continued
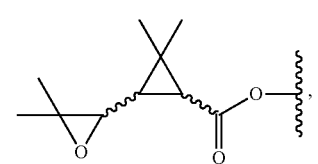 A10
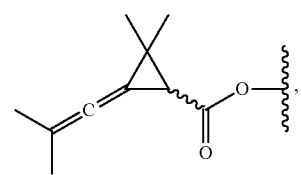 A11
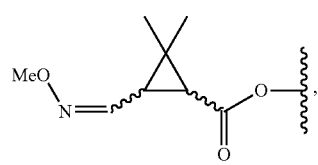 A12
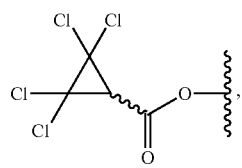 A13
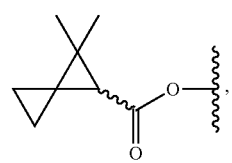 A14
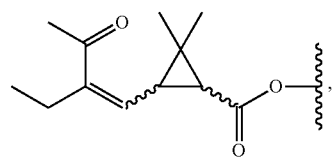 A15
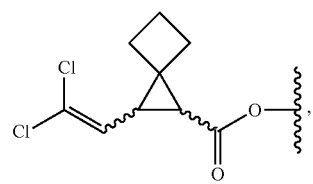 A16
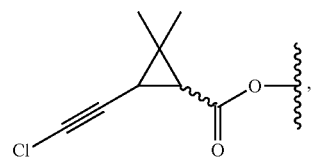 A17
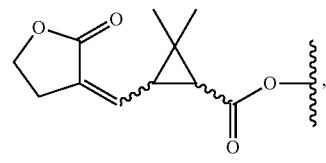 A18
-continued
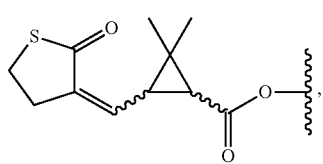 A19
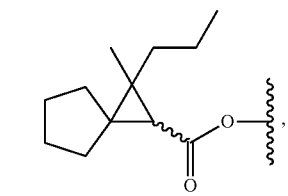 A20
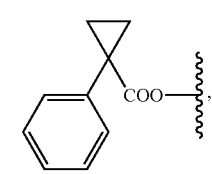 A21
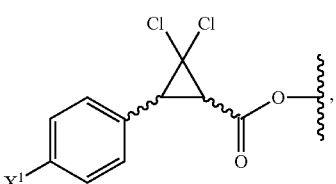 A22
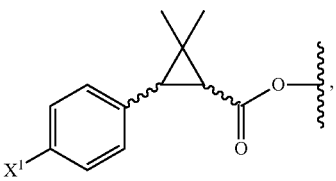 A23
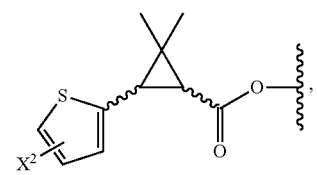 A24
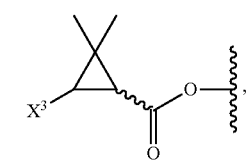 A25
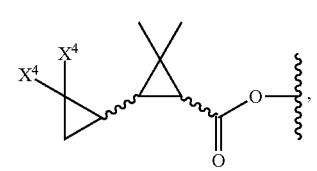 A26

-continued

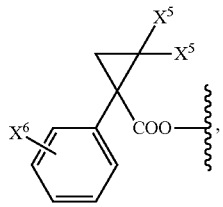
A27

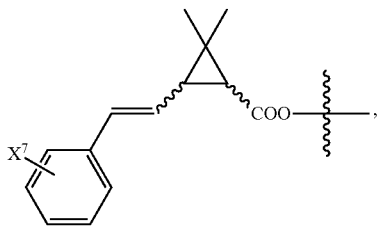
A28

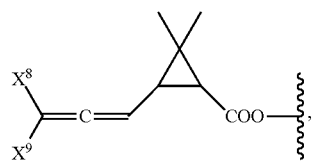
A29

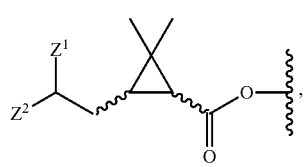
A30

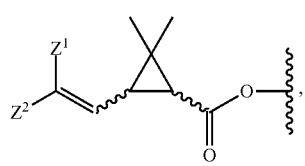
A31

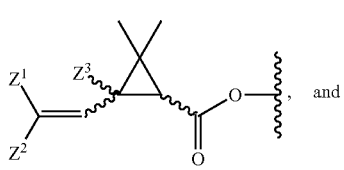
A32, and

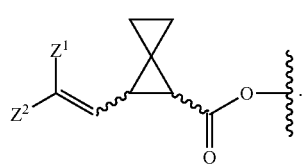
A33

For the A moieties listed above, $X^1$ is selected from H, optionally substituted $C_{1-6}$ alkyl, halo$C_{1-6}$ alkyl, optionally substituted $C_{1-6}$ alkoxy, halo$C_{1-6}$ alkyl, optionally substituted $C_{1-6}$ alkylthio, $C_{1-6}$ alkylsilyl, halo, and cyano. $X^2$ is selected from H, chloro, and methyl. $X^3$ is selected from H, methyl, halo, and CN. Each $X^4$ is independently halo. Each $X^5$ is independently selected from methyl and halo. $X^6$ is selected from halo, optionally substituted $C_{1-6}$ alkyl, and optionally substituted $C_{1-6}$ alkoxy. $X^7$ is selected from H, methyl, and halo. $X^8$ is selected from H, halo, and optionally substituted $C_{1-6}$ alkyl. $X^9$ is selected from H, halo, optionally substituted $C_{1-6}$ alkyl, C(O)O—($C_{1-6}$ alkyl), C(O)—N($C_{1-6}$ alkyl)$_2$, and cyano. $Z^1$, $Z^2$, and $Z^3$ are independently selected from H, halo, optionally substituted $C_{1-6}$ alkyl, and optionally substituted $C_{6-10}$ aryl, or $Z^1$ and $Z^2$ are taken together to form an optionally substituted 5- to 6-membered cycloalkyl or heterocyclyl group. The wavy line at the right of each structure represents the point of connection between the A moiety and a B moiety.

"B" moieties in the pyrethroids include, but are not limited to:

B1

B2

B3

B4

B5

B6

B7, and

B8

For the B moieties show above, the wavy line at the left of each structure represents the point of connection between the B moiety and an A moiety.

The methods of the invention can be used to prepare pyrethroids having any A moiety joined to any B moiety. A given pyrethroid can have a structure selected from: A1-B1; A2-B1; A3-B1; A4-B1; A5-B1; A6-B1; A7-B1; A8-B1; A9-B1; A10-B1; A11-B1; A12-B1; A13-B1; A14-B1; A15-

B1; A16-B1; A17-B1; A18-B1; A19-B1; A20-B1; A21-B1; A22-B1; A23-B1; A24-B1; A25-B1; A26-B1; A27-B1; A28-B1; A29-B1; A30-B1; A31-B1; A32-B1; A33-B1; A1-B2; A2-B2; A3-B2; A4-B2; A5-B2; A6-B2; A7-B2; A8-B2; A9-B2; A10-B2; A11-B2; A12-B2; A13-B2; A14-B2; A15-B2; A16-B2; A17-B2; A18-B2; A19-B2; A20-B2; A21-B2; A22-B2; A23-B2; A24-B2; A25-B2; A26-B2; A27-B2; A28-B2; A29-B2; A30-B2; A31-B2; A32-B2; A33-B2; A1-B3; A2-B3; A3-B3; A4-B3; A5-B3; A6-B3; A7-B3; A8-B3; A9-B3; A10-B3; A11-B3; A12-B3; A13-B3; A14-B3; A15-B3; A16-B3; A17-B3; A18-B3; A19-B3; A20-B3; A21-B3; A22-B3; A23-B3; A24-B3; A25-B3; A26-B3; A27-B3; A28-B3; A29-B3; A30-B3; A31-B3; A32-B3; A33-B3; A1-B4; A2-B4; A3-B4; A4-B4; A5-B4; A6-B4; A7-B4; A8-B4; A9-B4; A10-B4; A11-B4; A12-B4; A13-B4; A14-B4; A15-B4; A16-B4; A17-B4; A18-B4; A19-B4; A20-B4; A21-B4; A22-B4; A23-B4; A24-B4; A25-B4; A26-B4; A27-B4; A28-B4; A29-B4; A30-B4; A31-B4; A32-B4; A33-B4; A1-B5; A2-B5; A3-B5; A4-B5; A5-B5; A6-B5; A7-B5; A8-B5; A9-B5; A10-B5; A11-B5; A12-B5; A13-B5; A14-B5; A15-B5; A16-B5; A17-B5; A18-B5; A19-B5; A20-B5; A21-B5; A22-B5; A23-B5; A24-B5; A25-B5; A26-B5; A27-B5; A28-B5; A29-B5; A30-B5; A31-B5; A32-B5; A33-B5; A1-B6; A2-B6; A3-B6; A4-B6; A5-B6; A6-B6; A7-B6; A8-B6; A9-B6; A10-B6; A11-B6; A12-B6; A13-B6; A14-B6; A15-B6; A16-B6; A17-B6; A18-B6; A19-B6; A20-B6; A21-B6; A22-B6; A23-B6; A24-B6; A25-B6; A26-B6; A27-B6; A28-B6; A29-B6; A30-B6; A31-B6; A32-B6; A33-B6; A1-B7; A2-B7; A3-B7; A4-B7; A5-B7; A6- B7; A7-B7; A8-B7; A9-B7; A10-B7; A11-B7; A12-B7; A13-B7; A14-B7; A15-B7; A16-B7; A17-B7; A18-B7; A19-B7; A20-B7; A21-B7; A22-B7; A23-B7; A24-B7; A25-B7; A26-B7; A27-B7; A28-B7; A29-B7; A30-B7; A31-B7; A32-B7; A33-B7; A1-B8; A2-B8; A3-B8; A4-B8; A5- B8; A6-B8; A7-B8; A8-B8; A9-B8; A10-B8; A11-B8; A12-B8; A13-B8; A14-B8; A15-B8; A16-B8; A17-B8; A18-B8; A19-B8; A20-B8; A21-B8; A22-B8; A23-B8; A24-B8; A25-B8; A26-B8; A27-B8; A28-B8; A29-B8; A30-B8; A31-B8; A32-B8; and A33-B8. The A moiety is joined to the B moiety to form the ester bond as shown in Formula 2 above.

One of skill in the art will appreciate that a number of other pyrethroids can be prepared according to the methods of the invention, provided that the alcohol starting material contains a suitable unsaturated carbon-carbon bond for participation in the metathesis reaction with the olefin starting material.

Accordingly, a first aspect of the present invention provides a method for synthesizing a pyrethroid of Formula I:

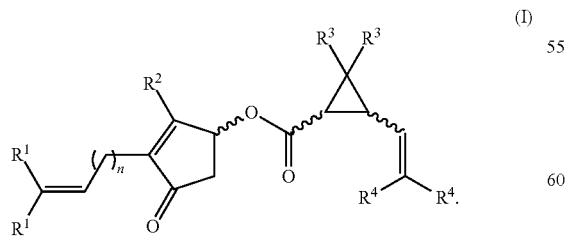

(I)

The method includes:

a) forming a first reaction mixture containing an olefin of Formula II:

(II)

and an alcohol of Formula III:

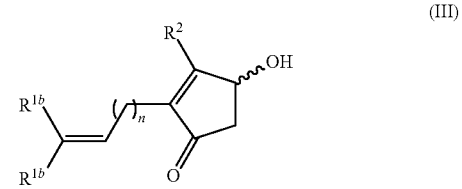

(III)

under conditions sufficient to form a metathesis product of Formula IV:

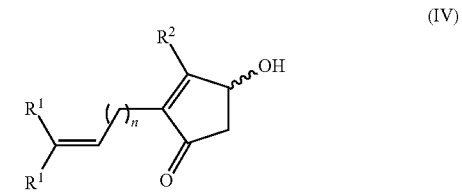

(IV)

and
b) converting the metathesis product to the pyrethroid;
wherein:
each $R^1$ and $R^2$ is independently selected from H, halo, $C_{1-12}$ alkyl, $C_{1-12}$ haloalkyl, $C_{1-12}$ alkoxy, $C_{1-12}$ alkenyl, $C_{1-12}$ haloalkenyl, $C_{1-12}$ alkenyloxy, and 3- to 6-membered heterocyclyl, wherein each alkyl, haloalkyl, alkoxy, alkenyl, haloalkenyl, and alkenyloxy group is optionally substituted with 1-5 substituents independently selected from hydroxy, $C_{1-6}$ alkoxy, and cyano;
each $R^{1a}$ and $R^{1b}$ is independently selected from H; halo; $C_{1-6}$ alkyl; $C_{1-6}$ haloalkyl; and $-O-SO_2R^c$, where $R^c$ is selected from $C_{1-6}$ alkyl, $C_{1-6}$ haloalkyl, and $C_{6-10}$ aryl;
each $R^3$ and $R^4$ is independently selected from H; $C_{1-18}$ alkyl; $C_{2-18}$ alkenyl; $C_{2-18}$ alkynyl; $C_{6-10}$ aryl optionally substituted with one or more $R^8$ groups; $C_1$-$C_6$ alkoxy optionally substituted with one or more $R^8$ groups; halo; hydroxy; cyano; $C(O)N(R^5)_2$; $NR^5C(O)R^6$; $C(O)R^6$; $C(O)OR^6$; and $N(R^7)_2$;
each $R^5$ and $R^6$ is independently selected from H; $C_{1-12}$ alkyl optionally substituted with one or more $R^8$ groups; $C_{2-12}$ alkenyl optionally substituted with one or more $R^8$ groups; and $C_{6-10}$ aryl optionally substituted with one or more $R^8$ groups;
each $R^7$ is independently selected from H; $C_{6-10}$ aryl optionally substituted with one or more $R^8$ groups; and 6- to 10-membered heteroaryl optionally substituted with one or more $R^8$ groups; or
two $R^7$ moieties, together with the nitrogen atom to which they are attached, form 6- to 18-membered heterocyclyl;
each $R^8$ is independently selected from halo, hydroxy, amino, alkylamino, alkoxy, haloalkyl, carboxy, amido, nitro, oxo, and cyano; and
the subscript n is 0 or 1.

Any suitable olefin can be used in the methods of the invention. In some embodiments, the olefin is selected from 1-propene; 1-butene; cis-2-butene; 1,3-butadiene; and (CH₂CH)—(CHX)—CH₃ or (CH₂CH)—(CH₂)—CH₂X, wherein X is halogen, tosylate, mesylate, or triflate. In some embodiments, the olefin is selected from 1-propene, 1-butene, cis-2-butene, 1,3-butadiene, 3-iodobut-1-ene, and 4-iodobut-1-ene.

Figure 4:
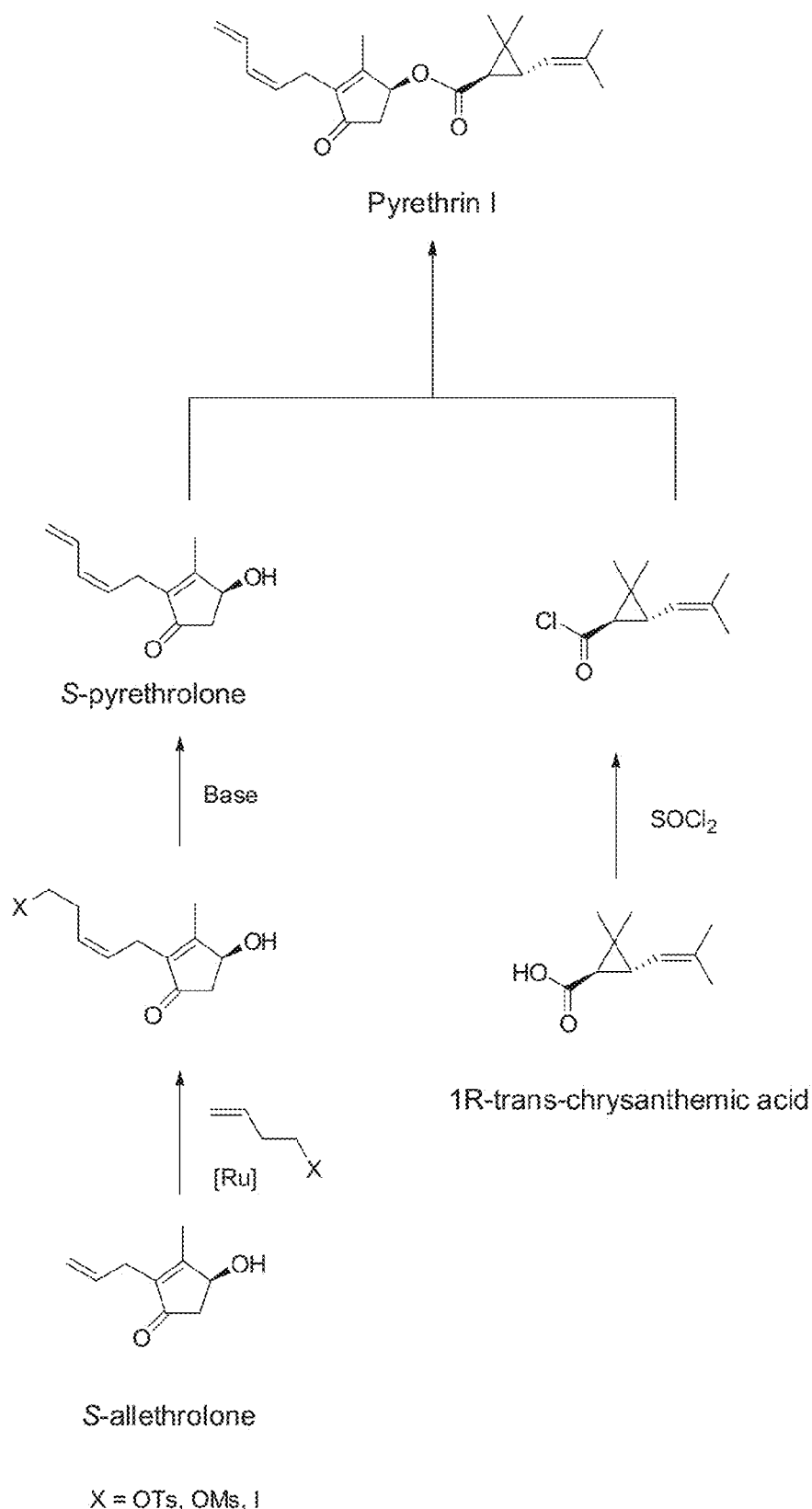
FIG. 4 shows a synthetic route for preparation of pyrethrin I according to the methods of the invention. [Ru] denotes the olefin metathesis catalyst.

In cases where the olefin of Formula II is halogenated (e.g., (CH₂CH)—(CHX)—CH₃ or (CH₂CH)—(CH₂)—CH₂X), the metathesis product of Formula III will be a halogenated olefin. See, for example, FIG. 4. In such cases, converting the metathesis product to the pyrethroid generally comprises dehydrohalogenating the metathesis product in the presence of a base. Any suitable base can be used in the methods of the invention. Examples of suitable bases include, but are not limited to, diisopropylamine, Huenig's base (i.e., diisopropylethylamine), lutidines including 2,6-lutidine (i.e., 2,6-dimethylpyridine), triethylamine, tributylamine, pyridine, 1,8-diazabicycloundec-7-ene (DBU), 1,5,7-triazabicyclo(4.4.0)dec-5-ene (TBD), 1,5-diazabicyclo[4.3.0]non-5-ene (DBN), 1,1,3,3-tetramethylguanidine (TMG), 2,2,6,6-tetramethylpiperidine (TMP), quinuclidine, potassium tert-butoxide, lithium diisopropylamide (LDA), lithium bis(trimethylsilyl)amide, and the collidines. Other bases can also be suitable in the methods of the invention. Combinations of two or more bases can be used.

The dehydrohalogenation reaction mixture can include any suitable amount of base. In general, the reaction mixture contains from about 1 to about 50 equivalents of base with respect to the metathesis product. In some embodiments, the reaction mixture contains from about 1 to about 5 equivalents of base with respect to the metathesis product. In some embodiments, the reaction mixture contains about 1.1 equivalents of base with respect to the metathesis product. In some embodiments, the reaction mixture contains about 1.1 equivalents of DBU, potassium tert-butoxide, LDA, diisopropylamine, triethylamine, lithium bis(trimethylsilyl)amide, or 2,6-dimethylpyridine with respect to the metathesis product. In some embodiments, the reaction mixture contains about 1.1 equivalents of DBU with respect to the metathesis product.

In general, converting the metathesis product to the pyrethroid involves esterifying a metathesis product as described above (or a dehydrohalogenated metathesis product) with a suitable carboxylic acid or carboxylic acid derivative. Examples of useful carboxylic acid derivatives include, but are not limited to, acid chlorides, acid anhydrides, and activated esters such as pentafluorophenyl esters and N-hydroxysuccinimidyl esters. Esterification reactions can be conducted using catalysts and/or coupling reagents such as carbodiimides (e.g., dicyclohexylcarbodiimide and N-(3-dimethylaminopropyl)-N'-ethylcarbodiimide), nucleophilic catalysts (e.g., N,N-dimethylaminopyridine), Lewis acids (e.g., copper (II) triflate), benzotriazoles, phosphonium reagents, uronium reagents, and formamidinium reagents. Methods for preparation of esters are known in the art as described, for example, by Ogliaruso and Wolfe ("Synthesis of Carboxylic Acids, Esters and Their Derivatives" *PATAI'S Chemistry of Functional Groups*, 1991, John Wiley & Sons Ltd.) and by Otera ("Reaction of Alcohols with Carboxylic Acids and Their Derivatives" *Esterification: Methods, Reactions, and Applications*, 2003, Wiley-VCH Verlag GmbH & Co. KGaA).

In some embodiments, converting the metathesis product to the pyrethroid includes forming a second reaction mixture containing the metathesis product and an esterification agent of Formula V:

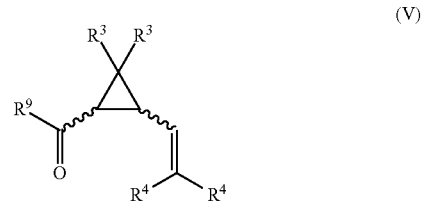

under conditions sufficient to form the pyrethroid, wherein $R^9$ is selected from halogen and —$OR^{9a}$, and $R^{9a}$ is selected from H, $C_{1-6}$ acyl, N-succinimidyl, and pentafluorophenyl. In some embodiments, $R^9$ in the esterification agent is chloro. In some embodiments, each $R^3$ in the esterification agent is methyl, one $R^4$ in the esterification agent is methyl, and the other $R^4$ in the esterification agent is methyl or —C(O)O-methyl. Esterification agents according to Formula V can be prepared using heme enzymes as described, for example, in U.S. Pat. No. 8,993,262, the disclosure of which is incorporated herein by reference in its entirety for all purposes.

The second reaction mixture (i.e., the esterification mixture) can include any suitable amount of esterification agent. In general, the esterification mixture contains at least about 1 equivalent of esterification agent with respect to the metathesis product. In some embodiments, the reaction mixture contains from about 1 to about 2 equivalents of esterification agent with respect to the metathesis product. In some embodiments, the reaction mixture contains about 1.1 equivalents of esterification agent with respect to the metathesis product. In some embodiments, the reaction mixture contains about 1.1 equivalents of an esterification agent of Formula V, wherein $R^9$ is chloro, with respect to the metathesis product.

In some embodiments, preparation of pyrethroids according to methods of the invention includes the conversion of S-allethrolone or derivatives thereof to the three types of alcohols found in pyrethrum via olefin metathesis (FIG. 1).

Figure 2:
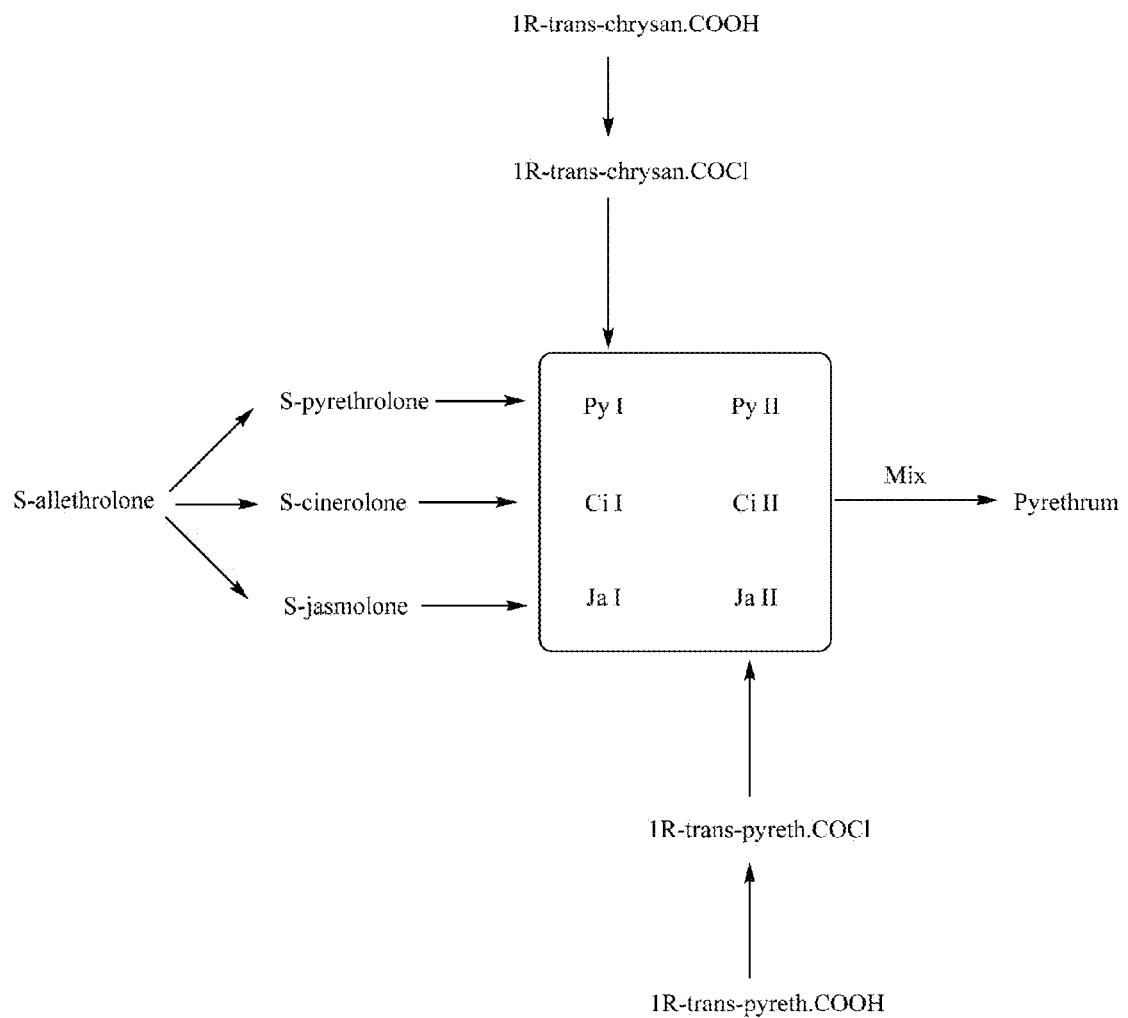
FIG. 2 shows the preparation of three alcohols (S-pyrethrolone, S-cinerolone and S-jasmolone) from S-allethrolone via olefin metathesis. The resulting alcohols can be esterified with 1R-trans-chrysanthemic acid chloride and 1R-trans-pyrethric acid chloride.

In some embodiments, the six pyrethrins of pyrethrum are synthesized from 1R-trans-chrysanthemic acid, 1R-trans-pyrethric acid, and S-allethrolone via (1) metathesis of S-allethrolone followed by (2) esterification of the resulting alcohols S-pyrethrolone, S-pyretholone, and S-jasmolone with 1R-trans-chrysanthemic acid and 1R-trans-pyrethric acid (FIG. 2).

Figure 3A:
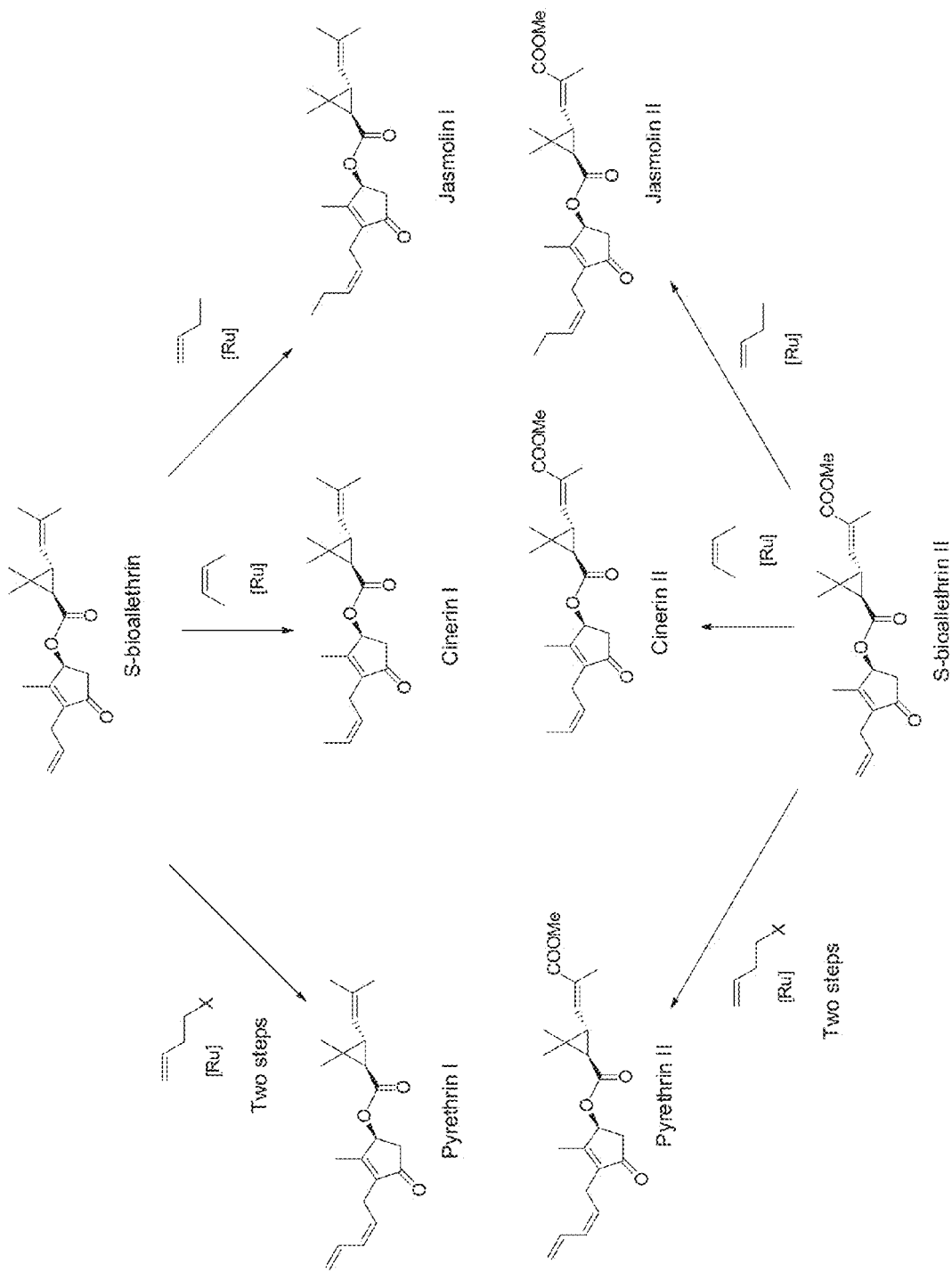
FIG. 3A shows a concise, metathesis-based route to all 6 pyrethrins starting directly from S-bioallethrin 1 and 2. [Ru] denotes the olefin metathesis catalyst.
Figure 3B:
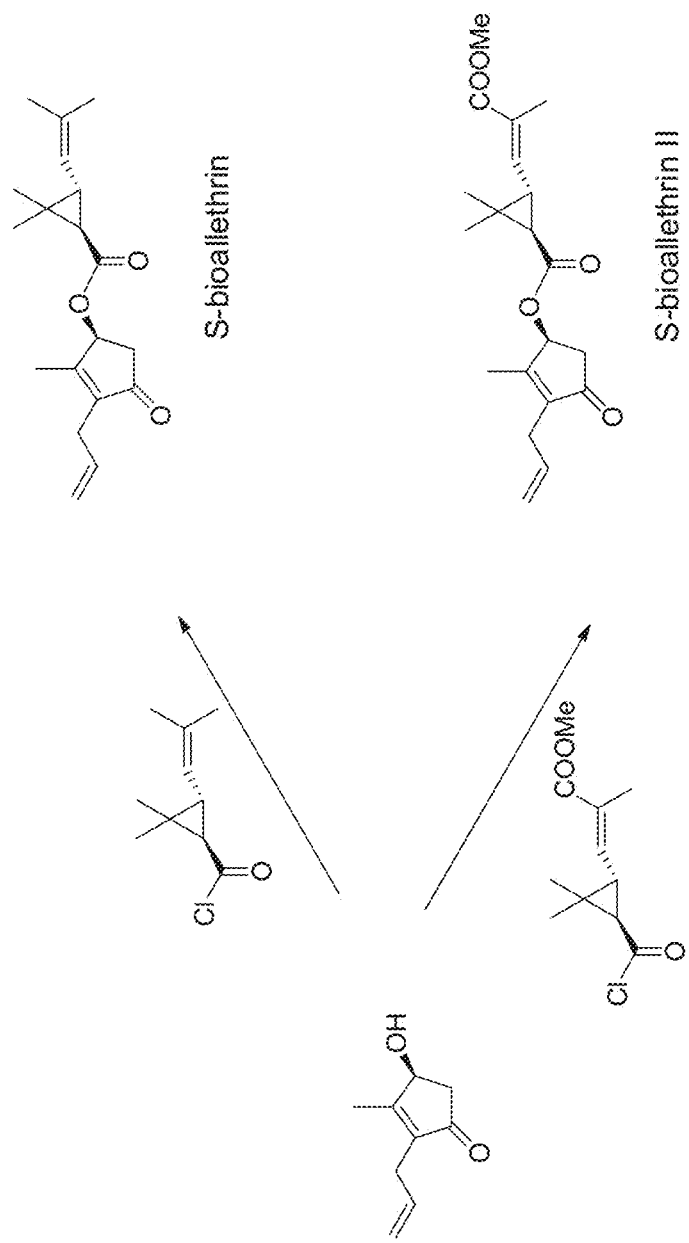
FIG. 3B shows the synthesis of S-bioallethrin 1 and 2 via esterification of S-allethrolone with 1R-trans-chrysanthemic acid chloride and 1R-trans-pyrethric acid chloride.

In some embodiments, the six pyrethrins of pyrethrum are synthesized from 1R-trans-chrysanthemic acid, 1R-trans-pyrethric acid, and S-allethrolone via (1) esterification of S-allethrolone with 1R-trans-chrysanthemic acid and 1R-trans-pyrethric acid, followed by (2) metathesis of S-bioallethrin I and II (FIG. 3).

Figure 5:
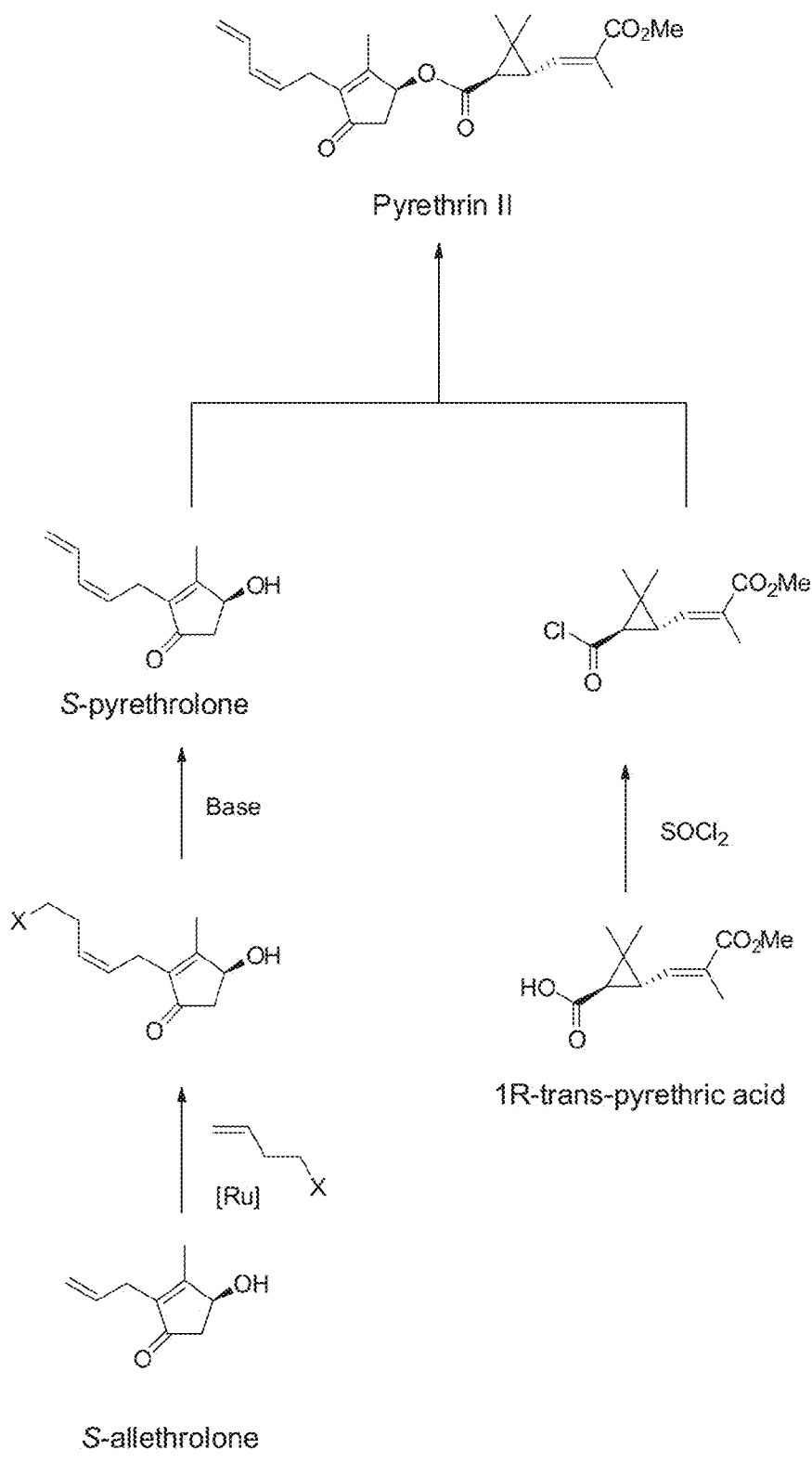
FIG. 5 shows a synthetic route for preparation of pyrethrin II according to the methods of the invention.
Figure 6:
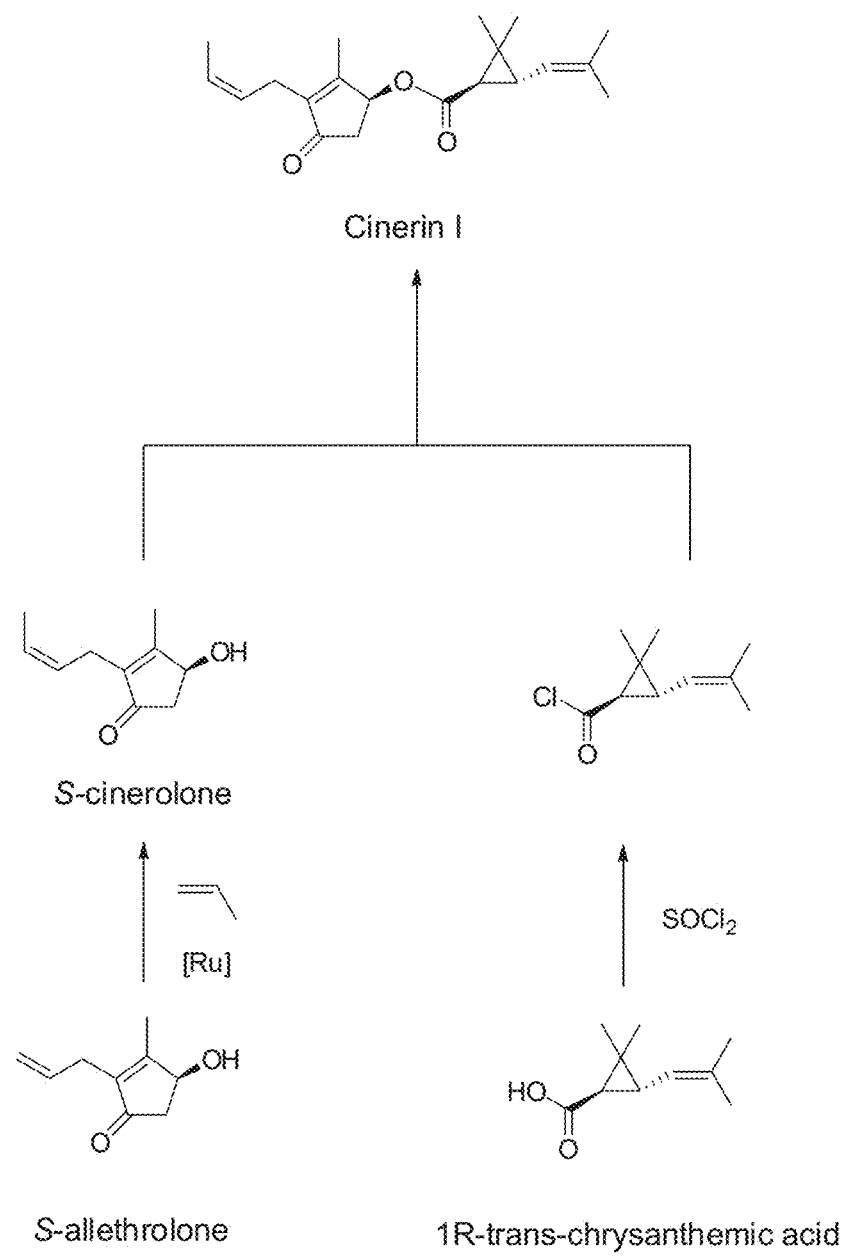
FIG. 6 shows a synthetic route for preparation of cinerin I according to the methods of the invention.
Figure 7:
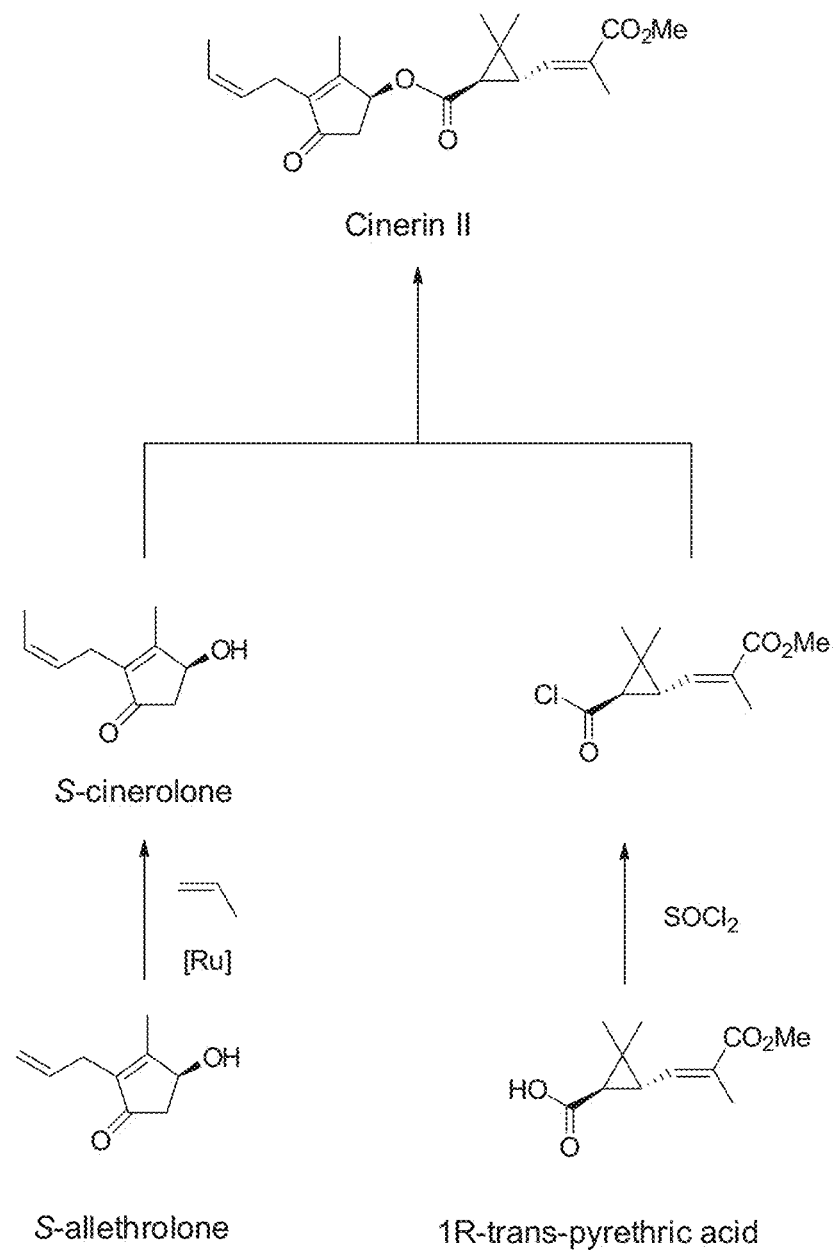
FIG. 7 shows a synthetic route for preparation of cinerin II according to the methods of the invention.
Figure 8:
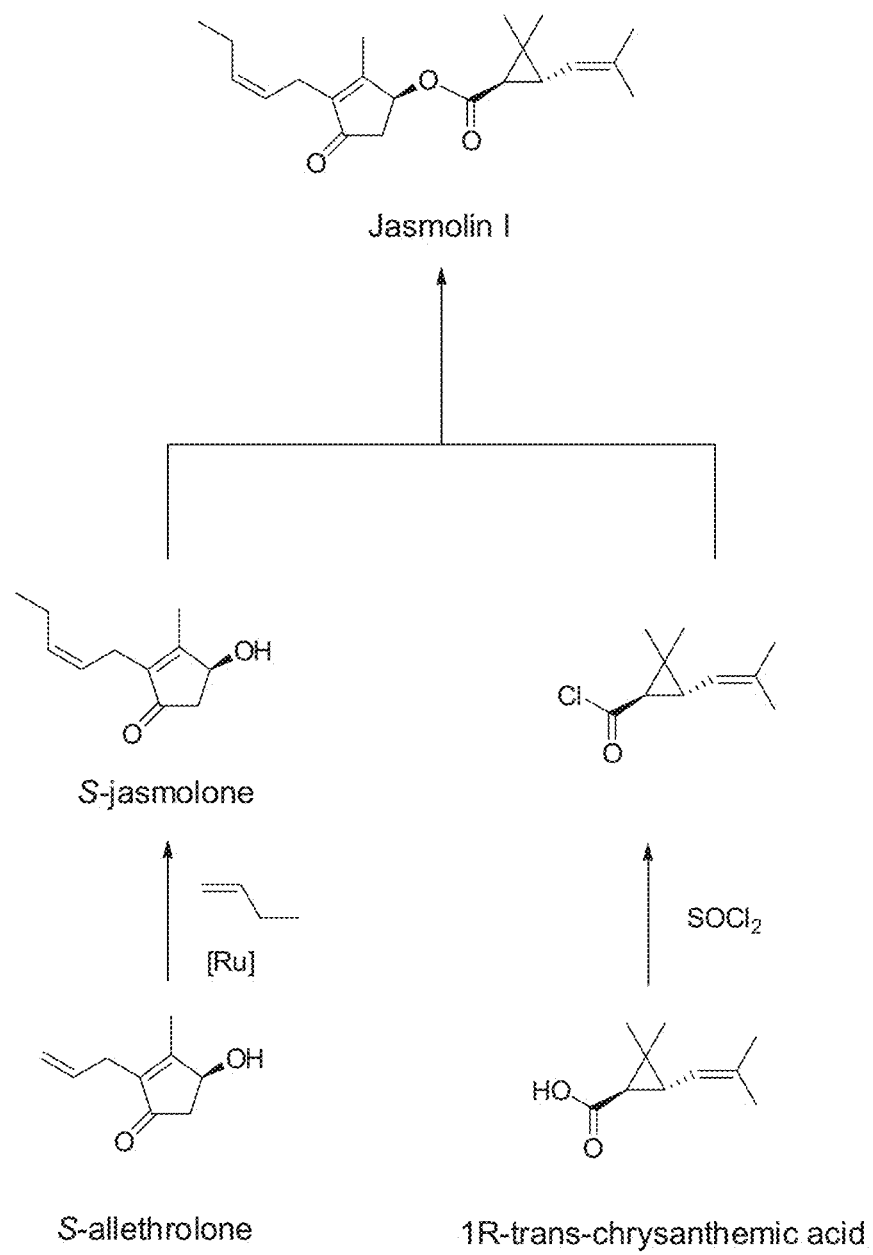
FIG. 8 shows a synthetic route for preparation of jasmolin I according to the methods of the invention.
Figure 9:
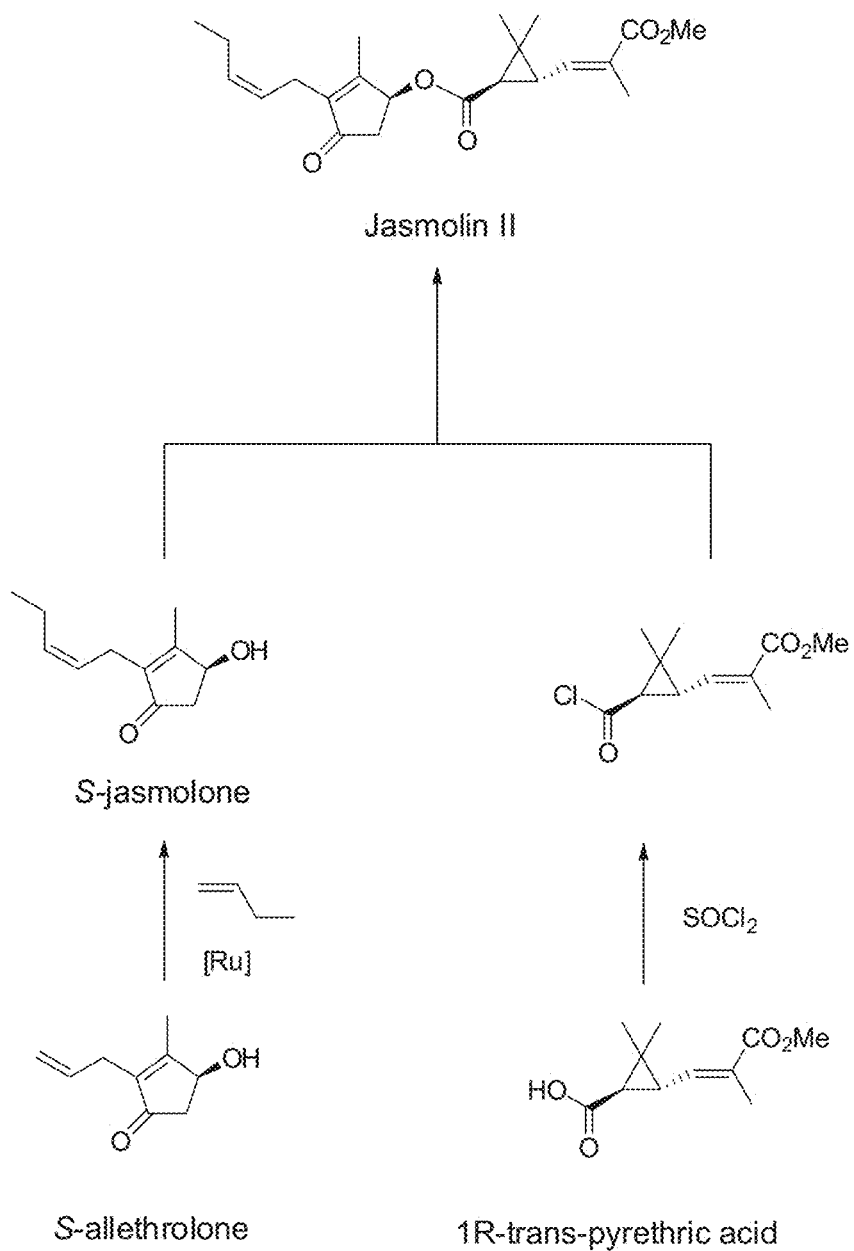
FIG. 9 shows a synthetic route for preparation of jasmolin II according to the methods of the invention.
Figure 10:
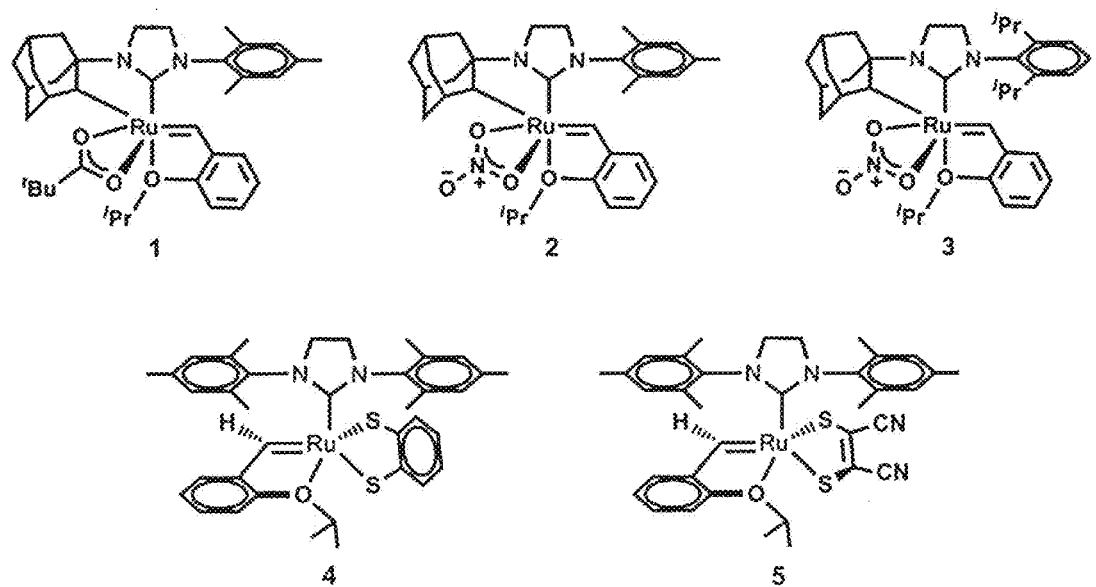
FIG. 10 shows metathesis catalysts that can be used in the methods of the invention.

Synthesis of pyrethroids from 1R-trans-chrysanthemic acid, 1R-trans-pyrethric acid, and S-allethrolone via (1) metathesis of S-allethrolone followed by (2) esterification with 1R-trans-chrysanthemic acid and 1R-trans-pyrethric acid is described for pyrethrin I (FIG. 4), pyrethrin II (FIG. 5), cinerin I (FIG. 6), cinerin II (FIG. 7), jasmolin I (FIG. 8), and jasmolin II (FIG. 9).

Accordingly, some embodiments of the invention provide methods for synthesizing a pyrethroid according to Formula I as described above wherein:
one $R^1$ is H and the other $R^1$ is selected from $C_{1-6}$ alkyl and $C_{1-6}$ alkenyl;
one $R^{1a}$ is H and the other $R^{1a}$ is selected from H, $C_{1-6}$ alkyl, and $C_{1-6}$ haloalkyl;
one $R^{1b}$ is H and the other $R^{1b}$ is selected from H, $C_{1-6}$ alkyl, and $C_{1-6}$ haloalkyl;
$R^2$ and each $R^3$ are $C_{1-6}$ alkyl;
one $R^4$ is $C_{1-6}$ alkyl and the other $R^4$ is selected from $C_{1-6}$ alkyl and $C(O)OR^6$, wherein $R^6$ is $C_{1-6}$ alkyl; and
subscript n is 1.

In some embodiments, the pyrethroid of Formula I is selected from:

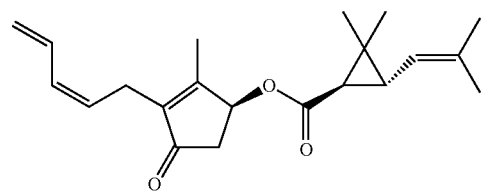

and

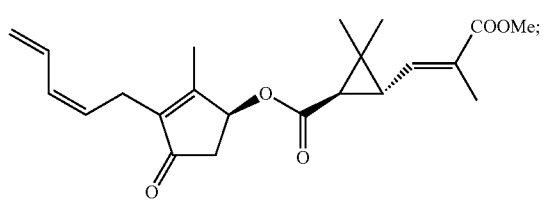

the olefin of Formula II is

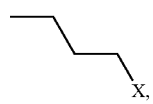

X, wherein X is halogen; and
the alcohol of Formula III is

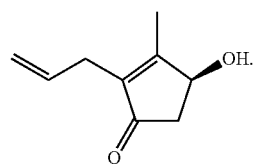

In some embodiments, the pyrethroid of Formula I is selected from

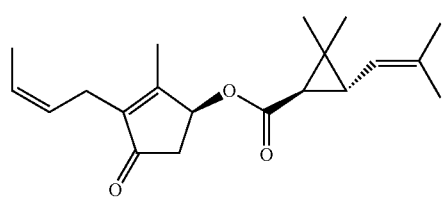

and

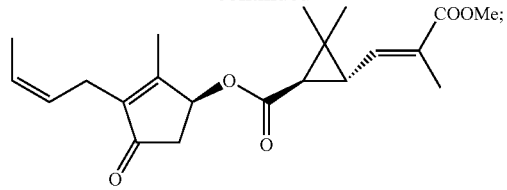

the olefin of Formula II is,

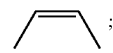

and the alcohol of Formula III is

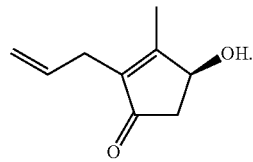

In some embodiments, the pyrethroid of Formula I is selected from

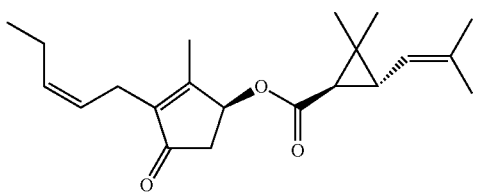

and

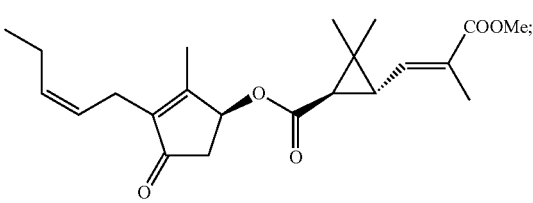

the olefin of Formula II is,

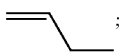

and the alcohol of Formula III is

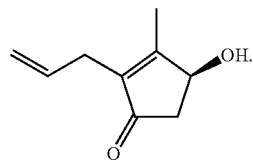

Typically, catalysts are used to prepare metathesis products of Formula IV, as well as other intermediates and products. In general, any metathesis catalyst stable under the reaction conditions and nonreactive with the functional groups present in the reactants shown in FIGS. 1-9 can be used in the methods of the invention. Suitable catalysts include, for example, those described by Grubbs (Grubbs, R. H., "Synthesis of large and small molecules using olefin metathesis catalysts." *PMSE Prepr.,* 2012). Depending on the desired isomer of the olefin, a cis-selective metathesis catalyst can be used, for example one of those described by Shahane et al. (Shahane, S., et al. *ChemCatChem,* 2013. 5(12): p. 3436-3459), herein incorporated by reference in its entirety. Specific catalysts 1-5 exhibiting cis-selectivity are shown below (Scheme 1) and have been described previously (Khan, R. K., et al. *J. Am. Chem. Soc.,* 2013. 135(28): p. 10258-61; Hartung, J. et al. *J. Am. Chem. Soc.,* 2013. 135(28): p. 10183-5; Rosebrugh, L. E., et al. *J. Am. Chem. Soc.,* 2013. 135(4): p. 1276-9; Marx, V. M., et al. *J. Am. Chem. Soc.,* 2013. 135(1): p. 94-7; Herbert, M. B., et al. *Angew. Chem. Int. Ed. Engl.,* 2013. 52(1): p. 310-4; Keitz, B. K., et al. *J. Am. Chem. Soc.,* 2012. 134(4): p. 2040-3; Keitz, B. K., et al. *J. Am. Chem. Soc.,* 2012. 134(1): p. 693-9; Endo, K. et al. *J. Am. Chem. Soc.,* 2011. 133(22): p. 8525-7).

Scheme 1

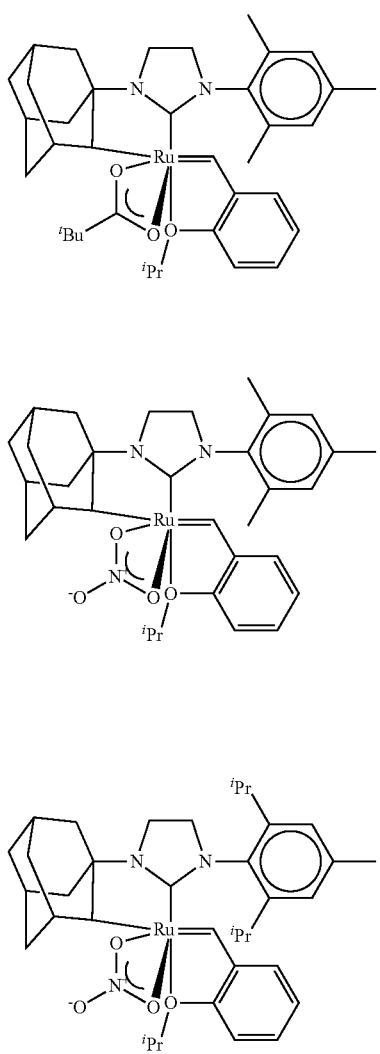

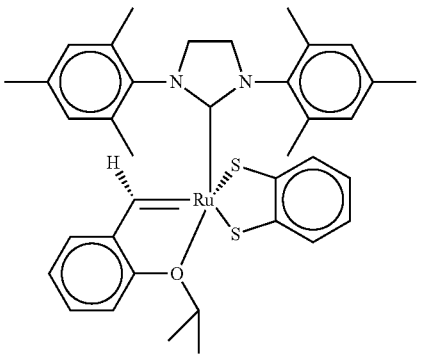

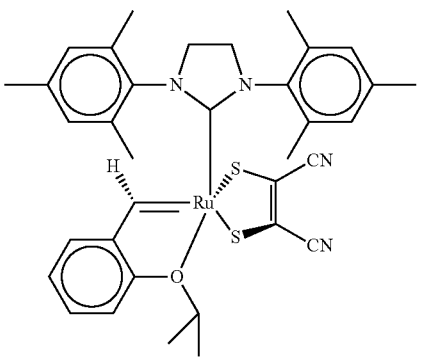

Additional Z-selective catalysts are described by Cannon et al. *Angew. Chemie Int. Ed.* 2013, 52: 9001-9004; Bronner et al. Chem. Sci. 2014, 5:4091-4098; Hartung et al. *J. Am. Chem. Soc.* 2014, 136: 13029-13037; Pribisko et al. *Polyhedron,* 2014, 84: 144-149; and Quigley et al. *Chem. Sci.,* 2014, 5: 501-506; which are incorporated herein by reference in their entirety. Due to their excellent stability and functional group tolerance, preferred metathesis catalysts include, but are not limited to, neutral ruthenium or osmium metal carbene complexes that possess metal centers that are formally in the +2 oxidation state, have an electron count of 16, are penta-coordinated, and are of the general formula $LL'AA'M=CR^bR^c$ or $LL'AA'M=(C=)_nCR^bR^c$; wherein M is ruthenium or osmium;

L and L' are each independently any neutral electron donor ligand and preferably selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes;

A and A' are anionic ligands independently selected from halogen, hydrogen, $C_1$-$C_{20}$ alkyl, aryl, $C_1$-$C_{20}$ alkoxide, aryloxide, $C_2$-$C_{20}$ alkoxycarbonyl, arylcarboxylate, $C_1$-$C_{20}$ carboxylate, arylsulfonyl, $C_1$-$C_{20}$ alkylsulfonyl, $C_1$-$C_{20}$ alkylsulfinyl; each ligand optionally being substituted with $C_1$-$C_5$ alkyl, halogen, $C_1$-$C_5$ alkoxy; or with a phenyl group that is optionally substituted with halogen, $C_1$-$C_5$ alkyl, or $C_1$-$C_5$ alkoxy; and A and A' together may optionally comprise a bidentate ligand; and $R^b$ and $R^c$ are independently selected from hydrogen, $C_1$-$C_{20}$ alkyl, aryl, $C_1$-$C_{20}$ carboxylate, $C_1$-$C_{20}$ alkoxy, aryloxy, $C_1$-$C_{20}$ alkoxycarbonyl, $C_1$-$C_{20}$ alkylthio, $C_1$-$C_{20}$ alkylsulfonyl and $C_1$-$C_{20}$ alkylsulfinyl, each of $R_b$ and $R_c$ optionally substituted with $C_1$-$C_5$ alkyl, halogen, $C_1$-$C_5$ alkoxy or with a phenyl group that is optionally substituted with halogen, $C_1$-$C_5$ alkyl, or $C_1$-$C_5$ alkoxy. See, Pedersen et al. *Angew. Chem. Int. Ed. Engl.* 2013, 52: 310-314.

Other metathesis catalysts such as "well defined catalysts" can also be employed. Such catalysts include, but are not limited to, Schrock's molybdenum metathesis catalyst, 2,6-diisopropylphenylimido neophylidenemolybdenum (VI) bis (hexafluoro-t-butoxide), described by Grubbs et al. (*Tetrahedron* 1998, 54: 4413-4450) and Basset's tungsten metathesis catalyst described in Couturier, J. L. et al. (*Angew. Chem. Int. Ed. Engl.* 1992, 31: 628).

Other metathesis catalysts such as "non-well defined catalysts" can also be employed, but their activity often requires the use of co-catalysts, which are typically heavy metals such as tetraalkyl tin or tetraalkyl lead compounds and present a waste disposal issue. These non-well defined catalysts can also require the presence of strong Lewis acids for activation, which may cause undesirable double bond migration.

Catalysts useful in the methods of the invention also include those described by Peryshkov, et al. *J. Am. Chem. Soc.* 2011, 133: 20754-20757; Wang, et al. *Angewandte Chemie*, 2013, 52: 1939-1943; Yu, et al. *J. Am. Chem. Soc.,* 2012, 134: 2788-2799; Halford. *Chem. Eng. News,* 2011, 89 (45): 11; Yu, et al. *Nature,* 2011, 479: 88-93; Lee. *Nature,* 2011, 471: 452-453; Meek, et al. *Nature,* 2011: 471, 461-466; Flook, et al. *J. Am. Chem. Soc.* 2011, 133: 1784-1786; Zhao, et al. *Org Lett.,* 2011, 13(4): 784-787; Ondi, et al. "High activity, stabilized formulations, efficient synthesis and industrial use of Mo- and W-based metathesis catalysts" *XiMo Technology Updates,* 2015: http://www.ximo-inc.com/files/ximo/uploads/download/Summary_3.11.15.pdf; Schrock, et al. *Macromolecules,* 2010: 43, 7515-7522; Peryshkov, et al. *Organometallics* 2013: 32, 5256-5259; Gerber, et al. *Organometallics* 2013: 32, 5573-5580; Marinescu, et al. *Organometallics* 2012: 31, 6336-6343; Wang, et al. *Angew. Chem. Int. Ed.* 2013: 52, 1939-1943; Wang, et al. *Chem. Eur. J.* 2013: 19, 2726-2740; and Townsend et al. *J. Am. Chem. Soc.* 2012: 134, 11334-11337.

Catalysts useful in the methods of the invention also include those described in International Pub. No. WO 2014/155185; International Pub. No. WO 2014/172534; U.S. Pat. Appl. Pub. No. 2014/0330018; International Pub. No. WO 2015/003815; and International Pub. No. WO 2015/003814.

Catalysts useful in the methods of the invention also include those described in U.S. Pat. No. 4,231,947; U.S. Pat. No. 4,245,131; U.S. Pat. No. 4,427,595; U.S. Pat. No. 4,681,956; U.S. Pat. No. 4,727,215; International Pub. No. WO 1991/009825; U.S. Pat. No. 5,087,710; U.S. Pat. No. 5,142,073; U.S. Pat. No. 5,146,033; International Pub. No. WO 1992/019631; U.S. Pat. No. 6,121,473; U.S. Pat. No. 6,346,652; U.S. Pat. Appl. Pub. No. 2008/0119678; International Pub. No. WO 2008/066754; International Pub. No. WO 2009/094201; U.S. Pat. Appl. Pub. No. 2011/0015430; U.S. Pat. Appl. Pub. No. 2011/0065915; U.S. Pat. Appl. Pub. No. 2011/0077421; International Pub. No. WO 2011/040963; International Pub. No. WO 2011/097642; U.S. Pat. Appl. Pub. No. 2011/0237815; U.S. Pat. Appl. Pub. No. 2012/0302710; International Pub. No. WO 2012/167171; U.S. Pat. Appl. Pub. No. 2012/0323000; U.S. Pat. Appl. Pub. No. 2013/0116434; International Pub. No. WO 2013/070725; U.S. Pat. Appl. Pub. No. 2013/0274482; U.S. Pat. Appl. Pub. No. 2013/0281706; International Pub. No. WO 2014/139679; International Pub. No. WO 2014/169014; U.S. Pat. Appl. Pub. No. 2014/0330018; and U.S. Pat. Appl. Pub. No. 2014/0378637.

Catalysts useful in the methods of the invention also include those described in International Pub. No. WO 2007/075427; U.S. Pat. Appl. Pub. No. 2007/0282148; International Pub. No. WO 2009/126831; International Pub. No. WO 2011/069134; U.S. Pat. Appl. Pub. No. 2012/0123133; U.S. Pat. Appl. Pub. No. 2013/0261312; U.S. Pat. Appl. Pub. No. 2013/0296511; International Pub. No. WO 2014/134333; and U.S. Pat. Appl. Pub. No. 2015/0018557.

Catalysts useful in the methods of the invention also include those set forth in Table 1.

TABLE 1

Metathesis catalysts.

| Structure | Name |
|---|---|
| 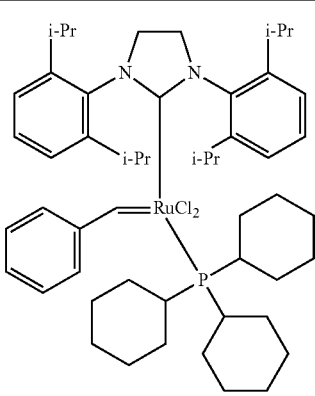 | dichloro[1,3-bis(2,6-isopropylphenyl)-2-imidazolidinylidene](benzylidene)(tricyclohexylphosphine)ruthenium(II) |

TABLE 1-continued

Metathesis catalysts.

| Structure | Name |
|---|---|
| 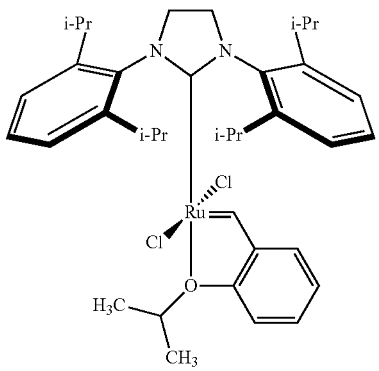 | dichloro[1,3-bis(2,6-isopropylphenyl)-2-imidazolidinylidene](2-isopropoxyphenylmethylene)ruthenium(II) |
| 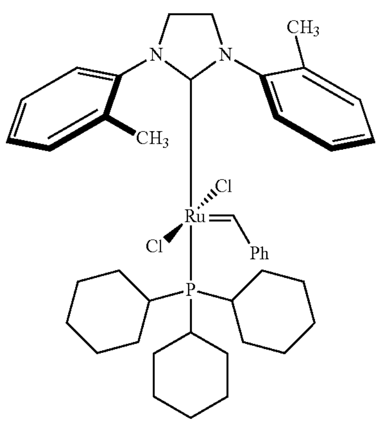 | dichloro[1,3-Bis(2-methylphenyl)-2-imidazolidinylidene](benzylidene)(tricyclohexylphosphine)ruthenium(II) |
| 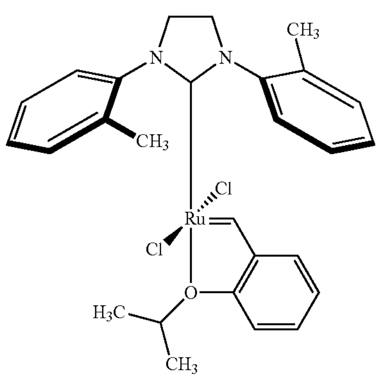 | dichloro[1,3-bis(2-methylphenyl)-2-imidazolidinylidene](2-isopropoxyphenylmethylene)ruthenium(II) |
| 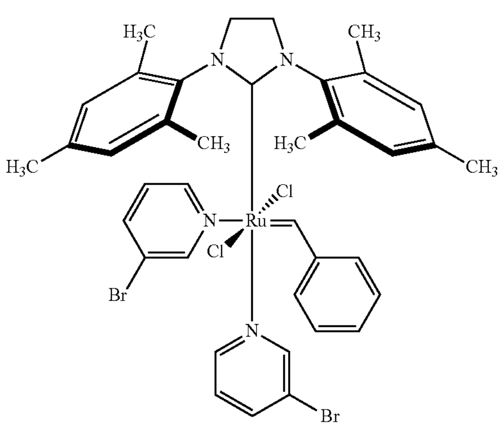 | dichloro[1,3-bis(2,4,6-trimethylphenyl)-2-imidazolidinylidene](benzylidene)bis(3-bromopyridine)ruthenium(II) |

TABLE 1-continued

Metathesis catalysts.

| Structure | Name |
|---|---|
| | dichloro[1,3-bis(2,4,6-trimethylphenyl)-2-imidazolidinylidene][(3-methyl-2-butenylidene)(tricyclohexylphosphine)ruthenium(II) |
| 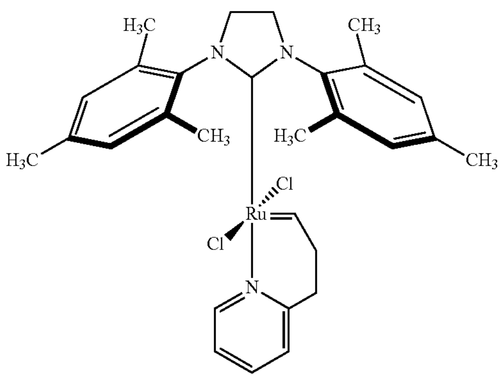 | dichloro[1,3-bis(2,4,6-trimethylphenyl)-2-imidazolidinylidene][3-(2-pyridinyl)propylidene]ruthenium(II) |
| 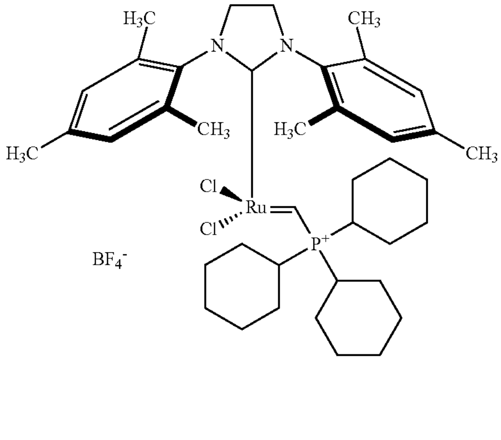 | dichloro[1,3-bis(2,4,6-trimethylphenyl)-2-imidazolidinylidene][(tricyclohexylphosphoranyl)methylidene]ruthenium(II) tetrafluoroborate |

TABLE 1-continued

Metathesis catalysts.

| Structure | Name |
|---|---|
| 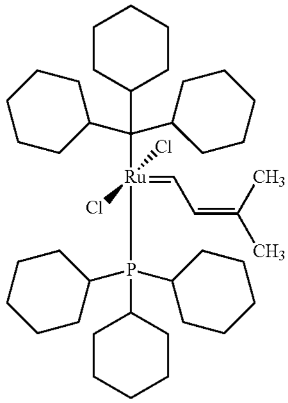 | dichloro(3-methyl-2-butenylidene) bis(tricyclohexylphosphine)ruthenium(II) |
| 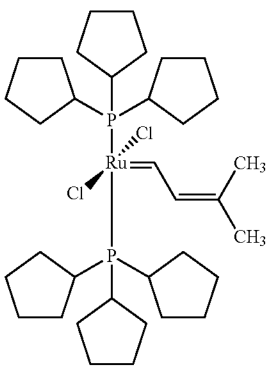 | dichloro(3-methyl-2-butenylidene) bis(tricyclopentylphosphine)ruthenium(II) |
| 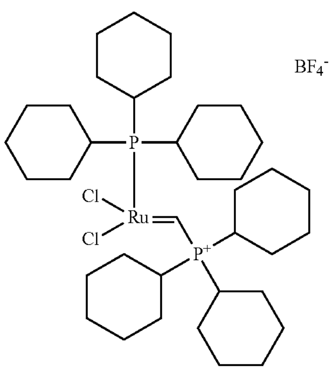 | dichloro(tricyclohexylphosphine) [(tricyclohexylphosphoranyl)methylidene] ruthenium(II) tetrafluoroborate |
| 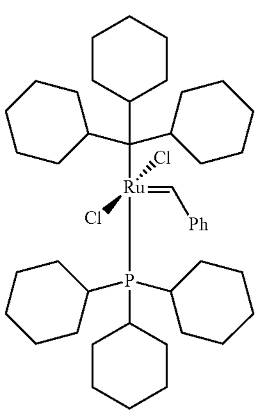 | bis(tricyclohexylphosphine)benzylidine ruthenium(IV)dichloride |

TABLE 1-continued

Metathesis catalysts.

| Structure | Name |
|---|---|
| 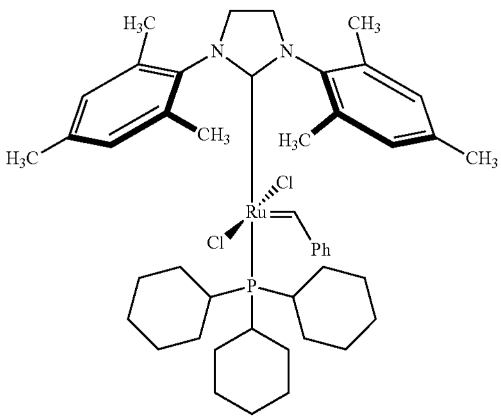 | [1,3-bis-(2,4,6-trimethylphenyl)-2-imidazolidinylidene]dichloro(phenylmethylene)(tricyclohexylphosphine)ruthenium |
| 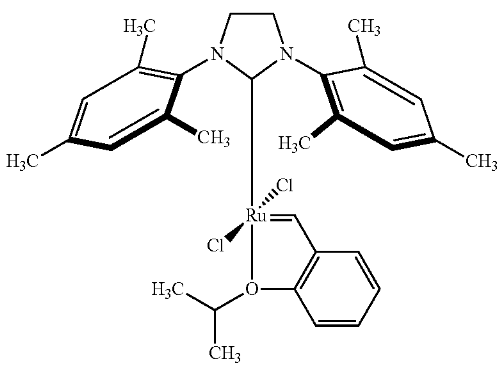 | (1,3-bis-(2,4,6-trimethylphenyl)-2-imidazolidinylidene)dichloro(o-isopropoxyphenylmethylene)ruthenium |
| 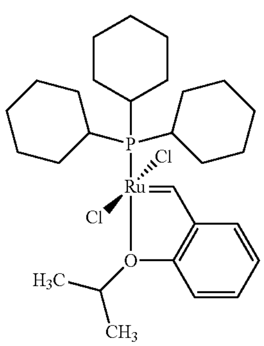 | dichloro(o-isopropoxyphenylmethylene)(tricyclohexylphosphine)ruthenium(II) |
| 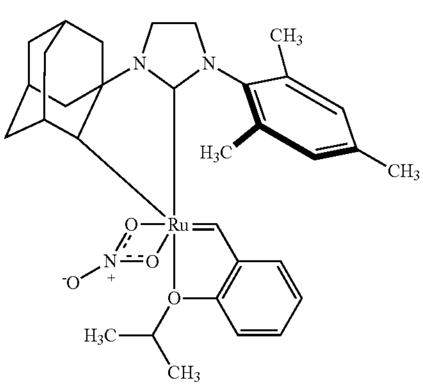 | [2-(1-methylethoxy-O)phenylmethyl-C](nitrato-O,O'){rel-(2R,5R,7R)-adamantane-2,1-diyl[3-(2,4,6-trimethylphenyl)-1-imidazolidinyl-2-y lidene]}ruthenium |

Catalysts useful in the methods of the invention also include those described in U.S. Pat. Appl. Pub. No. 2008/0009598; U.S. Pat. Appl. Pub. No. 2008/0207911; U.S. Pat. Appl. Pub. No. 2008/0275247; U.S. Pat. Appl. Pub. No. 2011/0040099; U.S. Pat. Appl. Pub. No. 2011/0282068; and U.S. Pat. Appl. Pub. No. 2015/0038723.

Catalysts useful in the methods of the invention include those described in International Pub. No. WO 2007/140954; U.S. Pat. Appl. Pub. No. 2008/0221345; International Pub. No. WO 2010/037550; U.S. Pat. Appl. Pub. No. 2010/0087644; U.S. Pat. Appl. Pub. No. 2010/0113795; U.S. Pat. Appl. Pub. No. 2010/0174068; International Pub. No. WO 2011/091980; International Pub. No. WO 2012/168183; U.S. Pat. Appl. Pub. No. 2013/0079515; U.S. Pat. Appl. Pub. No. 2013/0144060; U.S. Pat. Appl. Pub. No. 2013/0211096; International Pub. No. WO 2013/135776; International Pub. No. WO 2014/001291; International Pub. No. WO 2014/067767; U.S. Pat. Appl. Pub. No. 2014/0171607; and U.S. Pat. Appl. Pub. No. 2015/0045558.

The catalyst is typically provided in the reaction mixture in a sub-stoichiometric amount (e.g., catalytic amount). In certain embodiments, that amount is in the range of about 0.01 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

Accordingly, some embodiments of the invention provide methods of synthesizing pyrethroids as described above wherein the first reaction mixture comprises a metathesis catalyst. In some embodiments, the metathesis catalyst comprises ruthenium. In some embodiments, the metathesis catalyst is selected from:

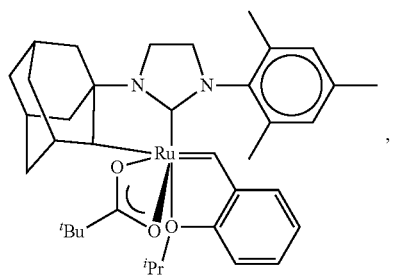

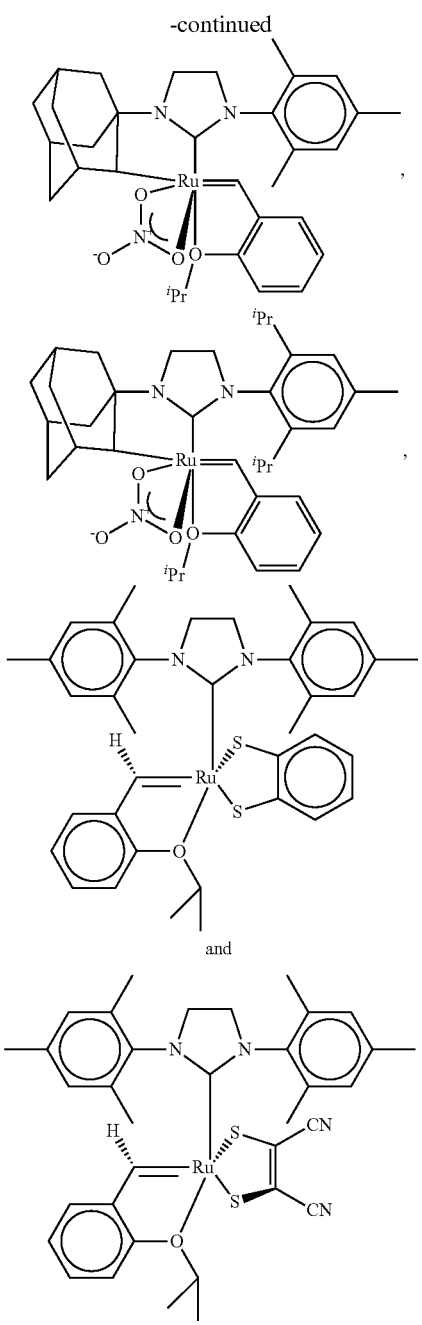

In some cases, the methods described herein can be performed in the absence of solvent (e.g., neat). In some cases, the methods can include the use of one or more solvents. Examples of solvents that may be suitable for use in the invention include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr.

In some embodiments, the method is performed at a pressure of about 19 torr. In some embodiments, the method is performed at a pressure of about 18 torr. In some embodiments, the method is performed at a pressure of about 17 torr. In some embodiments, the method is performed at a pressure of about 16 torr. In some embodiments, the method is performed at a pressure of about 15 torr. In some embodiments, the method is performed at a pressure of about 14 torr. In some embodiments, the method is performed at a pressure of about 13 torr. In some embodiments, the method is performed at a pressure of about 12 torr. In some embodiments, the method is performed at a pressure of about 11 torr. In some embodiments, the method is performed at a pressure of about 10 torr. In some embodiments, the method is performed at a pressure of about 10 torr. In some embodiments, the method is performed at a pressure of about 9 torr. In some embodiments, the method is performed at a pressure of about 8 torr. In some embodiments, the method is performed at a pressure of about 7 torr. In some embodiments, the method is performed at a pressure of about 6 torr. In some embodiments, the method is performed at a pressure of about 5 torr. In some embodiments, the method is performed at a pressure of about 4 torr. In some embodiments, the method is performed at a pressure of about 3 torr. In some embodiments, the method is performed at a pressure of about 2 torr. In some embodiments, the method is performed at a pressure of about 1 torr. In some embodiments, the method is performed at a pressure of less than about 1 torr.

In some embodiments, the two metathesis reactants are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the two reactants are present in a molar ratio of about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments, the two reactants are present in a molar ratio of about 1:10. In certain embodiments, the two reactants are present in a molar ratio of about 1:7. In certain embodiments, the two reactants are present in a molar ratio of about 1:5. In certain embodiments, the two reactants are present in a molar ratio of about 1:2.

In general, the reactions with many of the metathesis catalysts disclosed herein provide yields better than 15%, preferably better than 50%, more preferably better than 75%, and most preferably better than 90%. In addition, the reactants and products are chosen to provide at least a 5° C. difference, preferably a greater than 20° C. difference, and most preferably a greater than 40° C. difference in boiling points. Additionally, the use of metathesis catalysts typically allows for much faster product formation than byproduct, and it is desirable to run these reactions as quickly as practical. In particular, the reactions are performed in less than about 24 hours, preferably less than 12 hours, more preferably less than 8 hours, and most preferably less than 4 hours.

In a related second aspect, the invention provides a method for synthesizing a pyrethroid of Formula I:

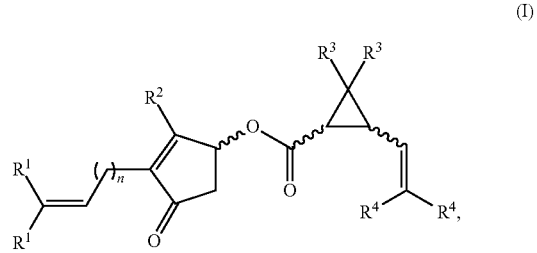

(I)

the method including:
a) forming a first reaction mixture containing an alcohol of Formula III:

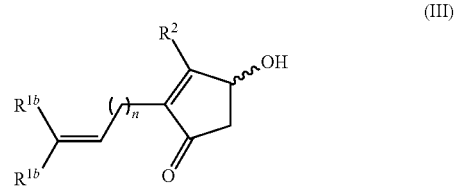

(III)

and an esterification agent of Formula V:

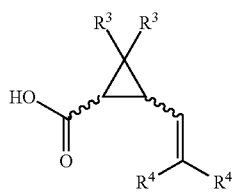
(V)

under conditions sufficient to form an ester of Formula VI:

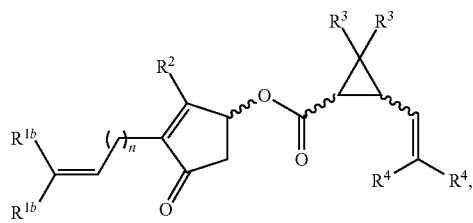
(VI)

and b) converting the ester to the pyrethroid;

wherein:

each $R^1$ and $R^2$ is independently selected from H, halo, $C_{1-12}$ alkyl, $C_{1-12}$ haloalkyl, $C_{1-12}$ alkoxy, $C_{1-12}$ alkenyl, $C_{1-12}$ haloalkenyl, $C_{1-12}$ alkenyloxy, and 3- to 6-membered heterocyclyl, wherein each alkyl, haloalkyl, alkoxy, alkenyl, haloalkenyl, and alkenyloxy group is optionally substituted with 1-5 substituents independently selected from hydroxy, $C_{1-6}$ alkoxy, and cyano;

each $R^{1b}$ is independently selected from H, halo, $C_{1-6}$ alkyl, and $C_{1-6}$ haloalkyl, each $R^3$ and $R^4$ is independently selected from H; $C_{1-18}$ alkyl; $C_{2-18}$ alkenyl; $C_{2-18}$ alkynyl; $C_{6-10}$ aryl optionally substituted with one or more $R^8$ groups; $C_1$-$C_6$ alkoxy optionally substituted with one or more $R^8$ groups; halo; hydroxy; cyano; $C(O)N(R^5)_2$; $NR^5C(O)R^6$; $C(O)R^6$; $C(O)OR^6$; and $N(R^7)_2$;

each $R^5$ and $R^6$ is independently selected from H; $C_{1-12}$ alkyl optionally substituted with one or more $R^8$ groups; $C_{2-12}$ alkenyl optionally substituted with one or more $R^8$ groups; and $C_{6-10}$ aryl optionally substituted with one or more $R^8$ groups;

each $R^7$ is independently selected from H; $C_{6-10}$ aryl optionally substituted with one or more $R^8$ groups; and 6- to 10-membered heteroaryl optionally substituted with one or more $R^8$ groups; or two $R^7$ moieties, together with the nitrogen atom to which they are attached, form 6- to 18-membered heterocyclyl;

each $R^8$ is independently selected from halo, hydroxy, amino, alkylamino, alkoxy, haloalkyl, carboxy, amido, nitro, oxo, and cyano; and the subscript n is 0 or 1.

In some embodiments of the second aspect, converting the ester to the pyrethroid includes forming a second reaction mixture containing the ester and an olefin of Formula II:

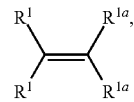
(II)

under conditions sufficient to form the pyrethroid; wherein each $R^{1a}$ is independently selected from H, halo, $C_{1-6}$ alkyl, and $C_{1-6}$ haloalkyl.

In some embodiments of the second aspect, converting the ester to the pyrethroid includes forming a second reaction mixture containing the ester and an olefin of Formula IIa:

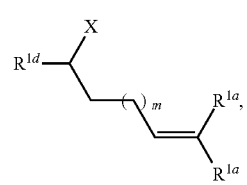
(IIa)

under conditions sufficient to form a pyrethroid according to Formula Ia:

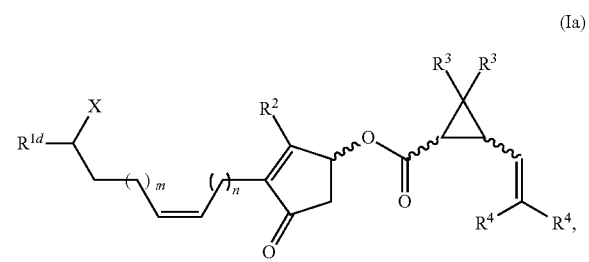
(Ia)

and converting the pyrethroid of Formula Ia to a pyrethroid of Formula Ib;

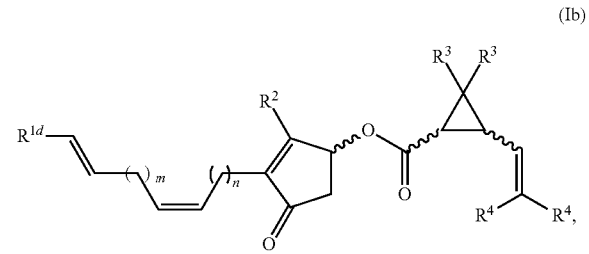
(Ib)

wherein each $R^{1a}$ is independently selected from H, halo, $C_{1-6}$ alkyl, and $C_{1-6}$ haloalkyl;

$R^{1d}$ is selected from H, $C_{1-9}$ alkyl, $C_{1-9}$ alkoxy, $C_{1-9}$ alkenyl, $C_{1-9}$ alkenyloxy, and 3- to 6-membered heterocyclyl;

X is halogen; and subscript m is an integer from 1 to 6.

In some embodiments of the second aspect, one $R^1$ is H and the other $R^1$ is selected from $C_{1-6}$ alkyl and $C_{1-6}$ alkenyl; one $R^{1a}$ is H and the other $R^{1a}$ is selected from H, $C_{1-6}$ alkyl, and $C_{1-6}$ haloalkyl; one $R^{1b}$ is H and the other $R^{1b}$ is selected from H, $C_{1-6}$ alkyl, and $C_{1-6}$ haloalkyl; $R^2$ and each $R^3$ are $C_{1-6}$ alkyl; one $R^4$ is $C_{1-6}$ alkyl and the other $R^4$ is selected from $C_{1-6}$ alkyl and $C(O)OR^6$, wherein $R^6$ is $C_{1-6}$ alkyl; and subscript n is 1.

In some embodiments of the second aspect, the esterification agent of Formula V is selected from:

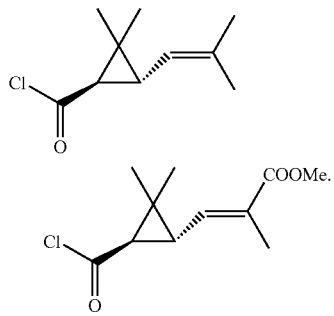

In some embodiments of the second aspect, the alcohol of Formula III is:

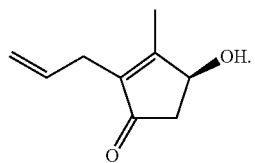

In some embodiments of the second aspect, the pyrethroid of Formula I is selected from:

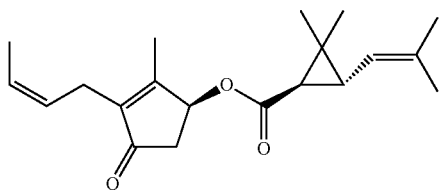

and

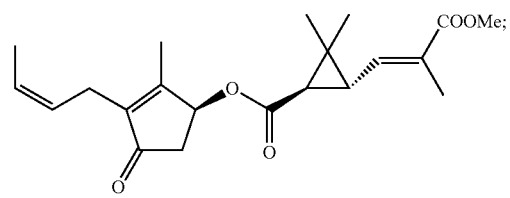

and the olefin of Formula II is

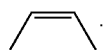

wherein X is halogen.

In some embodiments of the second aspect, the pyrethroid of Formula I is selected from

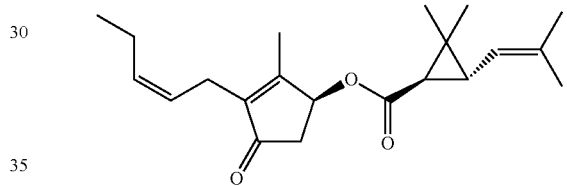

and

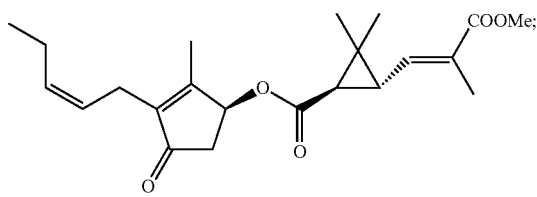

and the olefin of Formula II is

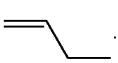

In some embodiments of the second aspect, the pyrethroid of Formula I is selected from

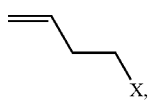

and and the olefin of Formula II is

In some embodiments of the second aspect, the second reaction mixture comprises a metathesis catalyst. In some embodiments of the second aspect, the metathesis catalyst comprises ruthenium.

One of skill in the art will appreciate that the metathesis, esterification, and dehydrohalogenation steps in the methods of the invention can be conducted using a variety of other solvents and reagents. Solvents useful in the methods of the invention include, but are not limited to, N-methyl pyrrolidinone (NMP), dimethylformamide (DMF), methylene chloride, chloroform, benzene, toluene, acetonitrile, tetrahydrofuran (THF), ether, dioxane, glyme, diglyme, ethyl acetate, methanol, ethanol and isopropanol. One of skill in the art will appreciate that other solvents and solvent combinations are useful in the present invention.

The metathesis, esterification, and dehydrohalogenation steps can proceed at a variety of temperatures and times. In general, reactions in the methods of the invention are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the invention are conducted at a temperature of from about 0° C. to about 200° C. For example, reactions can be conducted at 15-100° C. In some embodiments, reaction can be conducted at 20-80° C. In some embodiments, reactions can be conducted at 100-150° C. One of skill in the art will appreciate that the time, temperature and solvent can depend on each other, and that changing one can require changing the others to prepare the pyrethroid products and intermediates in the methods of the invention.

III. Mixtures of Pyrethrins

In another aspect, the invention provides insecticidal compositions containing pyrethroids prepared according to the methods described above. In general, an insecticidal composition of the invention contains at least one pyrethroid prepared according to the methods described above. In some embodiments, the insecticidal composition contains at least two, three, four, five, or six pyrethroids synthesized according to the methods described above.

Individual components of pyrethrum, prepared as described above, can be utilized as insecticides individually. In some embodiments, the six pyrethrins are mixed at a ratio resembling about the ratio of pyrethrins in their natural extracts as described by Glynne-Jones, (*Pesticide Outlook*, 2001. 12(5): p. 195-198), Maciver (in *Pyrethrum flowers: Production, Chemistry, Toxicology, and Uses*, 1995, Oxford University Press: New York. p. 108-121) and Head (in *Pyrethrum: The Natural Insecticide*, 1973, Academic Press: New York. p. 25-53), which are incorporated herein by reference in their entirety. Such mixtures are herein referred to as "nature-identical pyrethrum." Table 2 is reproduced from Glynne-Jones.

TABLE 2

| Composition of pyrethrum extract with respect to pyrethroid compounds. | |
|---|---|
| Ester | % w/w |
| Pyrethrin 1 | 38.0% |
| Pyrethrin 2 | 35.0% |
| Cinerin 1 | 7.4% |
| Cinerin 2 | 11.6% |
| Jasmolin 1 | 4.0% |
| Jasmolin 2 | 4.0% |
| Total | 100% |

In some embodiments, the % w/w of each of the individual components may vary from that described in Table 2 by 1%, 5%, 10%, 20%, 30%, 40%, 50%, 60%, 70%, 80%, or 90%.

In some embodiments, new mixtures that are not encompassed by any of the aforementioned embodiments may comprise any one of the six pyrethrins at any % w/w, ranging from 0-100%.

Accordingly, some embodiments of the invention provide compositions containing pyrethroid compound prepared according to the methods described above, wherein the composition contains:

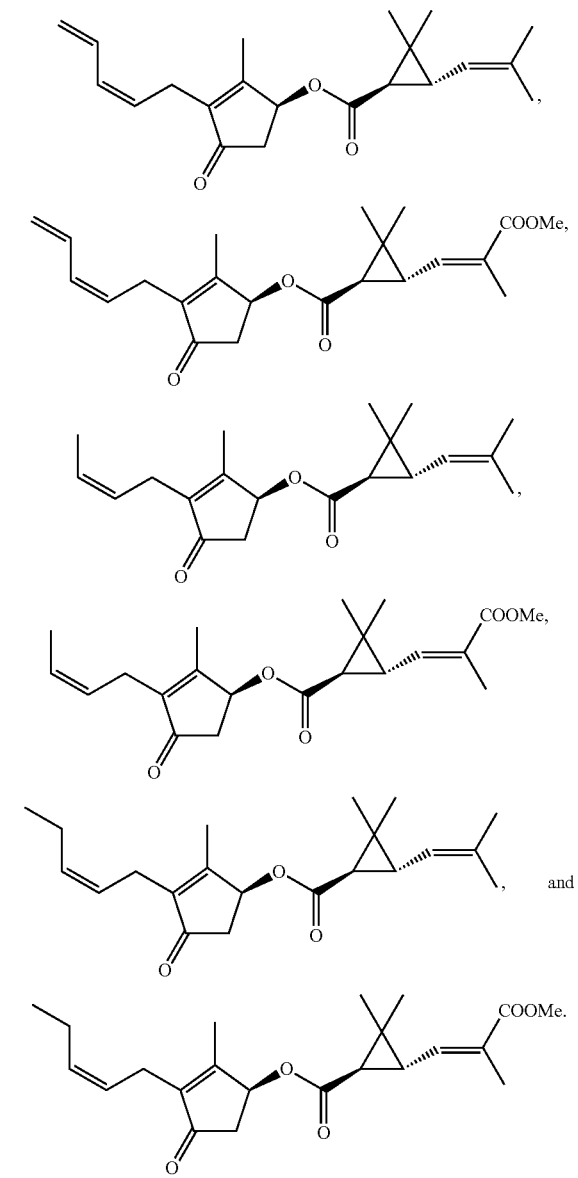

In some embodiment, the composition contains:

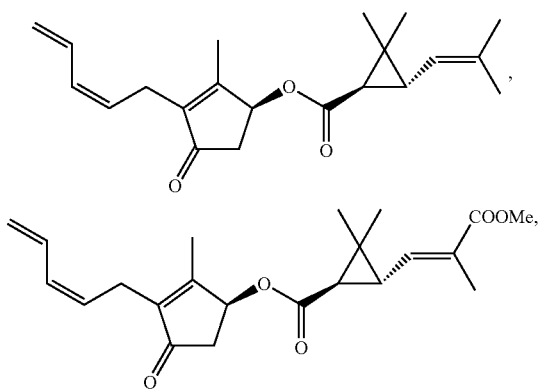

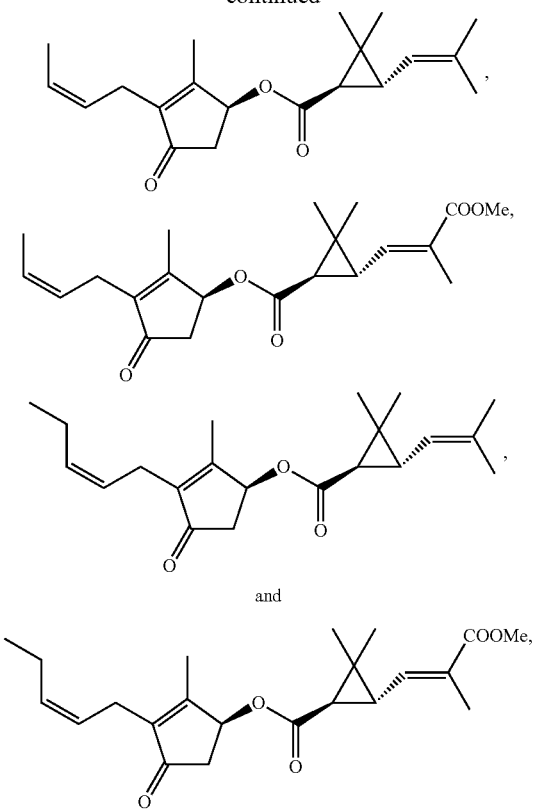

in a ratio of about 10:9:2:3:1:1 by weight.

In some embodiment, the composition contains:

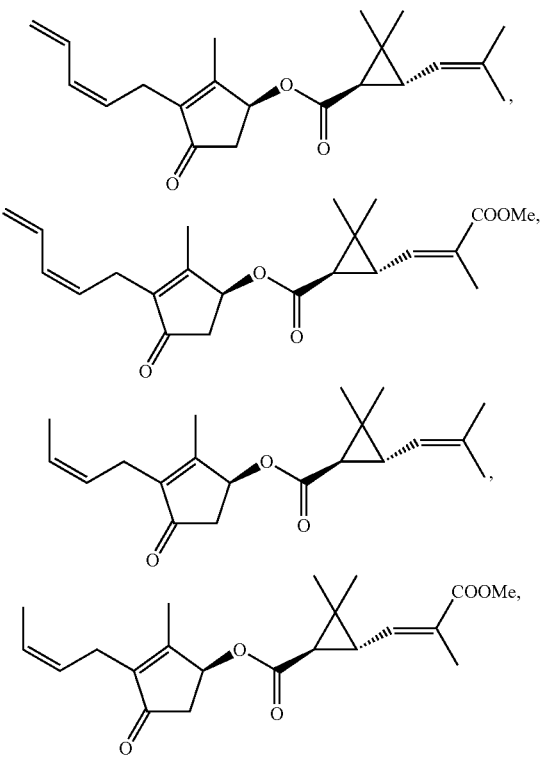

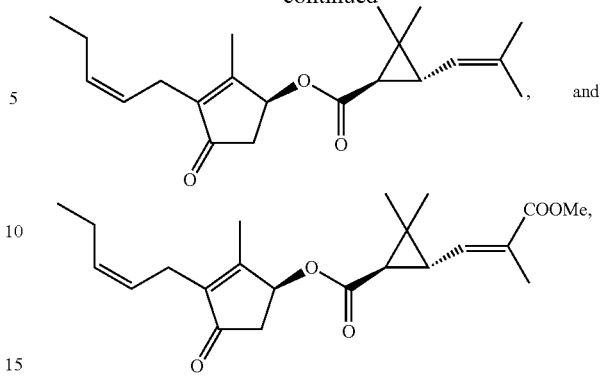

in a molar ratio of about 1:1:1:1:1:1.

IV. Formulations of Pyrethrins

Pyrethrin mixtures described above can be formulated in many different ways, for example as described by Casida, et al. (*Pyrethrum flowers: production, chemistry, toxicology, and uses.* 1995: Oxford Univ. Press. 356 pp; *Pyrethrum: The Natural Insecticide*, 1973, New York: Academic Press.), which references are incorporated herein by reference in their entirety.

Individual pyrethrins, mixtures thereof, including nature-identical pyrethrum can be utilized in an insecticidal aerosol formulation. Such a formulation typically contains a liquid consisting of pyrethrum between 0.01% (w/w) to 50% (w/w) dissolved in paraffin and a propellant usually consisting of a liquefied petroleum gas. The formulation may also include a synergist such as piperonyl butoxide, benzodioxoles, N-alkyl-5-norbornene-2,3-dicarboximides at synergist:pyrethrum ratios of 0.1:1 to 20:1. Examples of the paraffin are Isopar M, Isopar L, Isopar H, and mineral oil. The liquefied petroleum gas propellant can be, for example dimethyl ether, propane, butane, isobutane and mixtures thereof. The volume ratio of the base liquid to the liquefied petroleum gas can be 40:60 to 60:40. The delivery vessel should be a pressure-proof container equipped with an appropriate valve to produce droplets with average diameters of 1 μM to 50 μM (see, e.g., U.S. Pat. Appl. Pub. No. 2013/0005688, U.S. Pat. No. 4,295,581).

Individual pyrethrins, mixtures thereof, including nature-identical pyrethrum as well as other mixtures of pyrethrins can be formulated as a gel for use in vapor-producing systems utilizing a heat source. Such formulations contain pyrethrum at a defined composition with a combination of synergists, vaporization-controlling substances, gel forming inorganic compounds, antioxidants as stabilizers, perfume and colorants. The gel formulation can be prepared by stirring in a suitable mixing apparatus the pyrethrum with the desired combination of vaporization-controlling substances, antioxidants, perfumes, colorants and other solvents. When the mixture is homogenous, addition of the gel former under vacuum followed by rigorous stirring will produce the gel product. Vaporization-controlling substances can be and are not limited to (poly)aromatic and acyclic hydrocarbons in the pure form or as mixtures, diphenyl, diphenyl ether, o-, m-, p-terphenyl, mixtures of hydrogenated hydrocarbons and inorganic acid esters. Examples of these substances include Isopar V, Diphyl THT terphenyls, butyl stearate, butyl oleate, tricresyl phosphate. Examples of synergists include piperonyl butoxide, benzodioxoles, polychlorinated esters and N-alkyl-5-norbornene-2,3-dicaboximides. Gel formers can be highly-disperse silicas such as, Mox80 Aerosilox 50 150, Aerosil 200. Antioxidants that can be employed are all known UV absorbers, such as butylhydroxytolunene, butylhydroxyanisole, phenyl-α-naphthylamine, benzophenones. Colorant such as iron oxide, titanium oxide, alizarin dyes, azo dyes can be added for visual detection of the end of biological activity. Examples of perfumes that can be added include musk, almond oil, camphor oil, turpentine oil, absolution of vanilla. The solvents that can be used for the preparation of the gel formulation are all inert organic solvents. The formulation generally comprised between 0.1 and 95% by weight of pyrethrum, 1 and 90% by weight vaporization-controlling substances, 1 and 8% by weight gel formers (see, e.g., U.S. Pat. No. 5,645,845).

Individual pyrethrins, mixtures thereof, including nature-identical pyrethrum as well as other mixtures of pyrethrins can be absorbed onto mats, tablets or wicks of cellulose, cotton, ceramics and/or porous resins, which is then utilized for sustained and controlled release of the insecticide with the aid of a heat source. The pyrethrum is mixed with the absorbent material in a liquid state. Impregnation can take place at an elevated temperature e.g. 35-40° C. to increase absorption rate. The pyrethrum will be present in a weight percentage from 5% to 70%. In such a formulation, additional synergists, vapor-controlling substances, antioxidants, perfumes and colorants can also be added as described above. An example formulation can be the following: 31% (w/w) pyrethrum, 1% (w/w) 2,2'-methylene bis (6-tert-butyl-4-ethyl-phenyl), 0.1% (w/w) Cl solvent Blue 35, 0.1% (w/w) Isopropyl myristate, 4% (w/w) Isopar M, 1% (w/w) Ethanol, 0.5% (w/w) Denatonium Berizoate, 62% (w/w) Cellulose mat (see, e.g., WO 2011155823, U.S. Pat. No. 6,337,080).

V. Methods for Controlling Insects

The pyrethroid compounds prepared according to the methods described above, as well as compositions containing the pyrethroid compounds, can be used for controlling insects in a variety of settings. For example, pyrethroid compounds prepared according to the methods of the invention can be used for protecting important agronomic crops—such as cotton, soybeans, alfalfa, corn, leafy vegetables, snapbeans, and tomatoes—from attack by insects, particularly Lepidopterous, Homopterous, and Colepterous insects. Pyrethroid compounds prepared according to the methods of the invention can also be used for treatment of animals—including household pets such as cats and dogs, as well as livestock—infested with or otherwise affected by insects such as fleas, horn flies, face flies, stable flies, house flies, mosquitoes, lice, ticks, and mites. In addition, pyrethroid compounds prepared according to the methods of the invention can be used for controlling insects in human environments such as homes, offices, and storage facilities. For example, materials such as timber, wooden beams, boxes, pallets, containers, telephone poles, wood lagging, plywood, chipboard, joinery, polymers, adhesives, glues, paper and board, leather, and concrete can be treated with the pyrethroid compounds to prevent infestation by insects during and after construction of buildings.

Accordingly, another aspect of the invention provides methods for controlling insects. The methods include applying an effective amount of a pyrethroid compound prepared according to the methods described above, or a composition containing a pyrethroid compound prepared according to the methods described above, to a locus where control of insects is desired. Any suitable amount of pyrethroid composition can be used in the methods of the invention. In agricultural applications, for example, concentrations from about 0.01 grams of pyrethroid compound per hectare to about 5000 grams of pyrethroid compound per hectare can be used for controlling insects.

In some embodiments, the methods for controlling insects include applying an effective amount of a pyrethroid mixture to a locus where control of insects is desired, wherein the pyrethroid mixture contains:

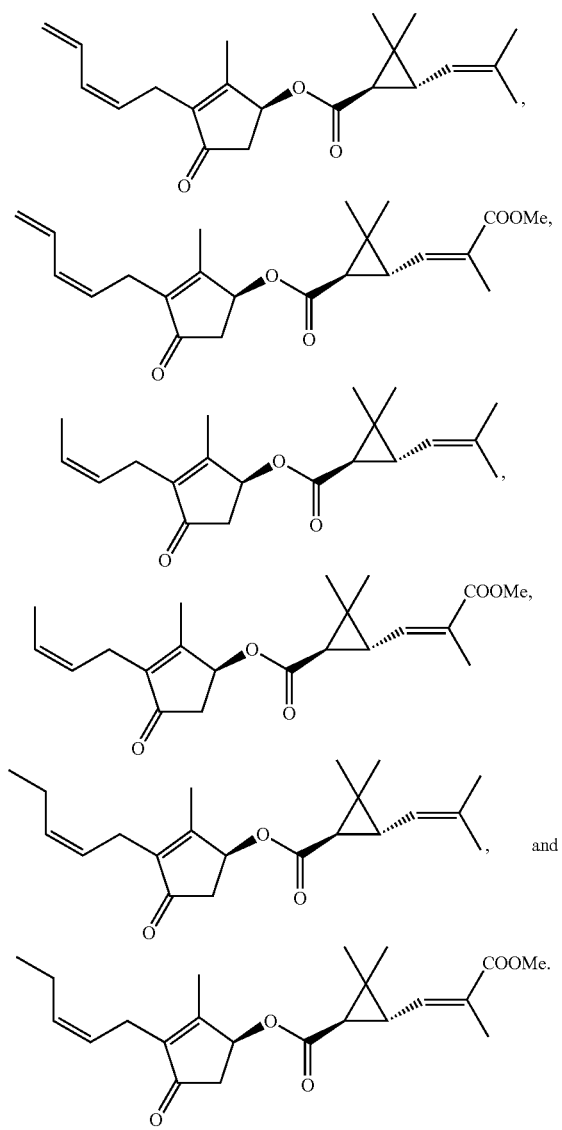

In certain instances, insects can develop resistance to pyrethroid compounds upon repeated exposure to a particular pyrethroid or a particular pyrethroid mixture. Methods of the invention can be conducted to prevent development of pyrethroid resistance by insects. Development of resistance can be inhibited or prevented by exposing insects to pyrethroid compositions that vary with respect to the particular pyrethroids in the compositions, or with respect to the amounts of pyrethroids in the compositions. The compositions can be varied at regular or irregular intervals over the course of application to a locus where control of insects is desired. Typically, intervals will vary in length from week to years.

Accordingly, some embodiments of the invention provide methods for controlling insects over multiple years. The methods include applying an effective amount of a composition containing pyrethroid compounds, prepared according to the methods above, to a locus where control of insects is desired. The composition contains:

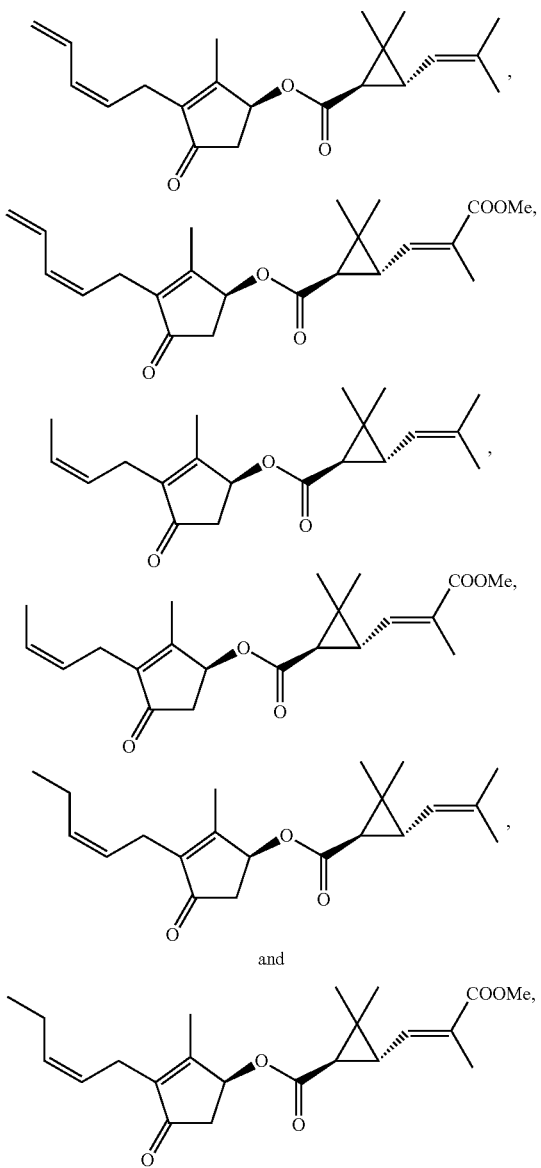
,

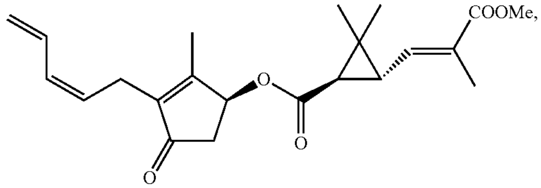

,

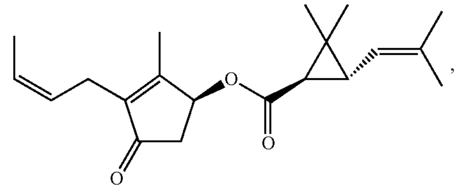

,

,

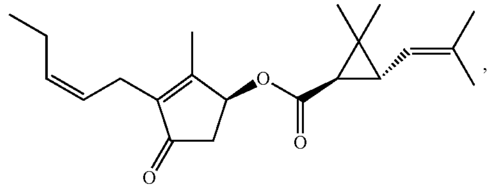

, and

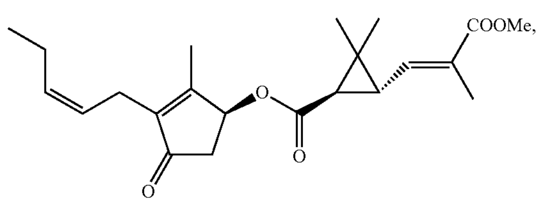

, which are varied in concentration from year to year.

For example, pyrethroid compositions can be applied to fields used for production of crops such as bell peppers (*Capsicum annuum*) and tomatoes (*Lycopersicon esculentum*) using the pyrethroid concentrations set forth in Table 3, a suitable carrier, and a suitable rate of application (e.g., 300 L/ha). Efficacy can be assessed by counting the insect populations in field plots, such as the number of whitefly (*Bemisia tabaci*) juveniles and adults on plant leaves. As a non-limiting example, varying the content of the compositions as shown in Table 3 can reduce the persistence of whiteflies and other pests and prevent re-infestation, when compared with methods employing the same composition from year to year.

TABLE 3

Compositions for long-term insect control.

| Compound | Year 1 | Year 2 | Year 3 | Year 4 | Year 5 |
|---|---|---|---|---|---|
| Pyrethrin 1 (% w/w) | 38.00% | 23.00% | 16.67% | 23.00% | 16.67% |
| Pyrethrin 2 (% w/w) | 35.00% | 20.00% | 16.67% | 20.00% | 16.67% |
| Cinerin 1 (% w/w) | 7.40% | 14.90% | 16.67% | 14.90% | 16.67% |
| Cinerin 2 (% w/w) | 11.60% | 15.10% | 16.67% | 15.10% | 16.67% |
| Jasmolin 1 (% w/w) | 4.00% | 13.50% | 16.67% | 13.50% | 16.67% |
| Jasmolin 2 (% w/w) | 4.00% | 13.50% | 16.67% | 13.50% | 16.67% |

VI. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Synthesis of Pyrethrin 1

Scheme 2

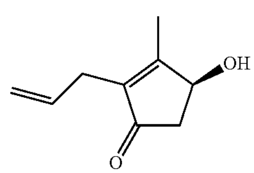

+

1-1
S-allethrolone 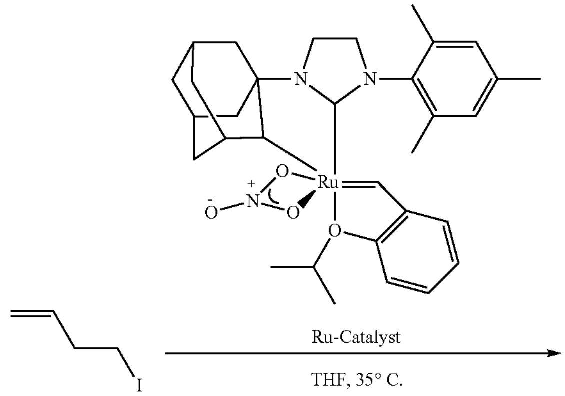 1-2

-continued

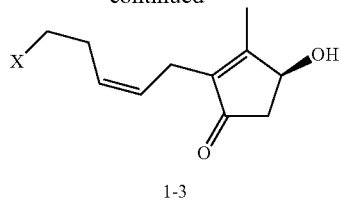

1-3

Compound 1-3 is prepared as shown in Scheme 2. Into a 100 mL two-necked round bottom flask, S-allethrolone 1-1 (10 g, 65.7 mmol), alkene 1-2 (35.8 g, 197.1 mmol), and THF are added, follow by the addition of Ru catalyst (0.21 g, 0.5 mol %). The reaction is then allowed to stir at 35° C. for 12 hours. The reaction solvent is removed under reduced pressure and the resulting residue is purified by chromatography using a mixture of hexane and ethyl acetate to obtain the desired product 1-3.

Scheme 3

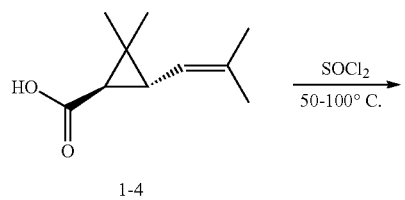

1-4

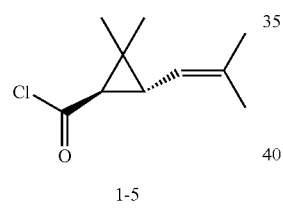

1-5

Compound 1-5 is prepared as shown in Scheme 3. Into a 250 mL two-necked round bottom flask equipped with an addition funnel and a reflux condenser, thionyl chloride (7.78 g, 65.42 mmol) is added. The reaction flask is gently heated at 50° C. and 1R-trans-chrysanthemic acid, 1-4, (10 g, 59.48 mmol) is then added dropwise to the reaction flask via the addition funnel. Upon complete addition of the acid, the reaction mixture is allowed to stir at 100° C. for another 30 min. The desired product, 1R-trans-chrysanthemyl chloride, is then isolated by distillation or silica gel chromatography.

Scheme 4

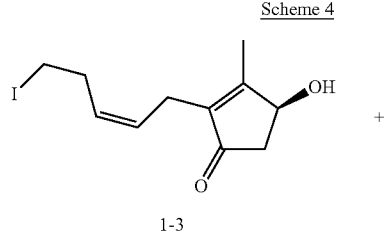

1-3

-continued

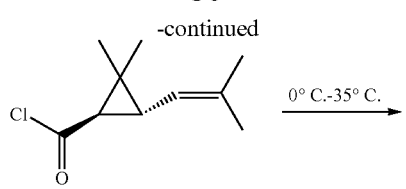

1-5

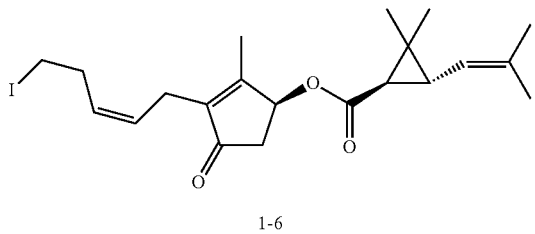

1-6

Compound 1-6 is prepared as shown in Scheme 4. Alcohol 3 (10 g, 32.6 mmol) is placed in a 250-mL two-necked flask equipped with a reflux condenser and addition funnel. With stirring, the reaction flask is cooled to 0° C. in an ice bath and 1R-trans-chrysanthemyl chloride 1-5 is added dropwise to the alcohol solution via the addition funnel. Upon complete addition of the acid chloride, the reaction mixture is allowed to warm to ambient temperature and is stirred for 1 hour. The reaction is quenched with 10 mL of water and extracted with ethyl acetate. The organic fraction is dried with anhydrous sodium sulphate, filtered through a Whatman filter paper, and concentrated to dryness under reduced pressure. The desired product 1-6 is then isolated by flash chromatography or by distillation.

Scheme 5

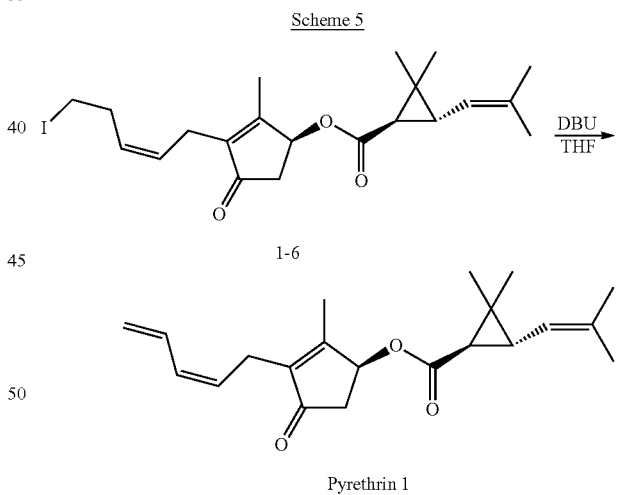

Pyrethrin 1 is prepared according to Scheme 5. Into a 250 mL two-necked round bottom flask equipped with a dropping funnel, 1,8-diazabicyclo[5.4.0]undec-7-ene (DBU) (3.67 g, 24.1 mmol) is dissolved in THF and then cooled to 0° C. in an ice bath. Compound 6 (10 g, 21.9 mmol) dissolved in THF is added dropwise to the DBU solution and the reaction mixture is allowed to react until all of compound 6 is converted to pyrethrin 1, as monitored by TLC. The reaction is quenched with water and extracted with ethyl acetate. The organic fraction is dried with sodium sulfate and concentrated to dryness. Pyrethrin 1 is then isolated by distillation or silica gel chromatography.

Example 2

Synthesis of Cinerin 1

Scheme 6

![Scheme 6 structures]

1-1
S-allethrolone

+

2-2

Ru-Catalyst
THF, 35° C.

2-3

Compound 2-3 is prepared as shown in Scheme 6. Into a 100 mL two-necked round bottom flask, S-allethrolone 1-1 (10 g, 65.7 mmol), alkene 2-2 (8.29 g, 197.1 mmol), and THF are added. Ru catalyst (0.21 g, 0.5 mol %) is then added and the reaction is allowed to stir at 35° C. for 12 hours. The reaction solvent is then removed in vacuo to provide a crude reaction product that is further purified by flash chromatography using a mixture of hexane and ethyl acetate to obtain the desired product, S-pyretholone 2-3.

Scheme 7

2-3

+

1-5

0° C.-35° C.

2-6

Compound 2-6 is prepared as shown in Scheme 7. Into a 250 mL two-necked flask equipped with a reflux condenser and dropping funnel, alcohol 2-3 (32.6 mmol) is added. The reaction flask is then cooled to in an ice bath. With stirring, 1R-trans-chrysanthemyl chloride 1-5, prepared as set forth in Example 1, is added dropwise to the alcohol 2-3. Upon complete addition of the acid chloride, the reaction mixture is allowed to warm to ambient temperature and stir for another hour. The reaction is quenched with 10 mL of water and extracted with ethyl acetate. The organic fraction is dried with anhydrous sodium sulphate, filtered through a Whatman filter paper and concentrate to dryness in vacuo. The desired product, 2-6 is then isolated by flash chromatography or distillation.

Pyrethrin II and cinerin II can be prepared as described for pyrethrin I and cinerin I in Examples 1 and 2, using 1R-trans-pyrethric acid (i.e., (1R,3R)-3-((E)-3-methoxy-2-methyl-3-oxoprop-1-en-1-yl)-2,2-dimethylcyclopropanecarboxylic acid) in place of 1R-trans-chrysanthemic acid.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of synthesizing a pyrethroid of Formula I:

(I)

the method comprising:

a) forming a first reaction mixture comprising an olefin of Formula II:

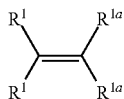

(II)

and an alcohol of Formula III:

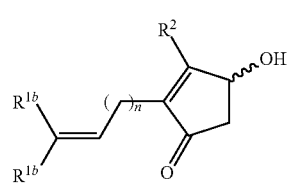

(III)

under conditions sufficient to form a metathesis product of Formula IV:

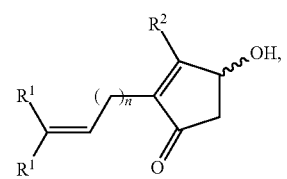

(IV)

and b) converting the metathesis product to the pyrethroid; wherein:

each $R^1$ and $R^2$ is independently selected from the group consisting of H, halo, $C_{1-12}$ alkyl, $C_{1-12}$ haloalkyl, $C_{1-12}$ alkoxy, $C_{1-12}$ alkenyl, $C_{1-12}$ haloalkenyl, $C_{1-12}$ alkenyloxy, and 3- to 6-membered heterocyclyl, wherein each alkyl, haloalkyl, alkoxy, alkenyl, haloalkenyl, and alkenyloxy group is optionally substituted with 1-5 substituents independently selected from the group consisting of hydroxy, $C_{1-6}$ alkoxy, and cyano;

each $R^{1a}$ and $R^{1b}$ is independently selected from the group consisting of H; halo; $C_{1-6}$ alkyl; $C_{1-6}$ haloalkyl; and —O—SO$_2$R$^c$, wherein R$^c$ is selected from the group consisting of $C_{1-6}$ alkyl, $C_{1-6}$ haloalkyl, and $C_{6-10}$ aryl;

each $R^3$ and $R^4$ is independently selected from the group consisting of H; $C_{1-18}$ alkyl; $C_{2-18}$ alkenyl; $C_{2-18}$ alkynyl; $C_{6-10}$ aryl optionally substituted with one or more $R^8$ groups; $C_1$-$C_6$ alkoxy optionally substituted with one or more $R^8$ groups; halo; hydroxy; cyano; C(O)N(R$^5$)$_2$; NR$^5$C(O)R$^6$; C(O)R$^6$; C(O)OR$^6$; and N(R$^7$)$_2$;

each $R^5$ and $R^6$ is independently selected from the group consisting of H; $C_{1-12}$ alkyl optionally substituted with one or more $R^8$ groups; $C_{2-12}$ alkenyl optionally substituted with one or more $R^8$ groups; and $C_{6-10}$ aryl optionally substituted with one or more $R^8$ groups;

each $R^7$ is independently selected from H; $C_{6-10}$ aryl optionally substituted with one or more $R^8$ groups; and 6- to 10-membered heteroaryl optionally substituted with one or more $R^8$ groups; or two $R^7$ moieties, together with the nitrogen atom to which they are attached, form 6- to 18-membered heterocyclyl;

each $R^8$ is independently selected from the group consisting of halo, hydroxy, amino, alkylamino, alkoxy, haloalkyl, carboxy, amido, nitro, oxo, and cyano; and the subscript n is 0 or 1.

2. The method of claim 1, wherein converting the metathesis product to the pyrethroid comprises dehydrohalogenating the metathesis product in the presence of a base.

3. The method of claim 1, wherein converting the metathesis product to the pyrethroid comprises forming a second reaction mixture comprising the metathesis product and an esterification agent of Formula V:

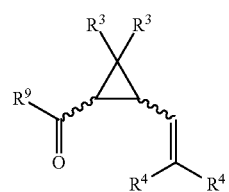

(V)

under conditions sufficient to form the pyrethroid, wherein $R^9$ is selected from the group consisting of halogen and —OR$^{9a}$, wherein $R^{9a}$ is selected from the group consisting of H, $C_{1-6}$ acyl, N-succinimidyl, and pentafluorophenyl.

4. The method of claim 3, wherein $R^9$ is chloro.

5. The method of claim 3, wherein each $R^3$ is methyl, one $R^4$ is methyl, and the other $R^4$ is methyl or —C(O)O-methyl.

6. The method of claim 1, wherein one $R^1$ is H and the other $R^1$ is selected from the group consisting of $C_{1-6}$ alkyl and $C_{1-6}$ alkenyl;

one $R^{1a}$ is H and the other $R^1$ is selected from the group consisting of H, $C_{1-6}$ alkyl, and $C_{1-6}$ haloalkyl;

one $R^{1b}$ is H and the other $R^{1b}$ is selected from the group consisting of H, $C_{1-6}$ alkyl, and $C_{1-6}$ haloalkyl;

$R^2$ and each $R^3$ are $C_{1-6}$ alkyl;

one $R^4$ is $C_{1-6}$ alkyl and the other $R^4$ is selected from the group consisting of $C_{1-6}$ alkyl and C(O)OR$^6$, wherein $R^6$ is $C_{1-6}$ alkyl; and subscript n is 1.

7. The method of claim 1, wherein the alcohol of Formula III is

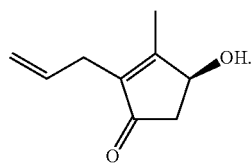

8. The method of claim 1, wherein the pyrethroid of Formula I is selected from the group consisting of

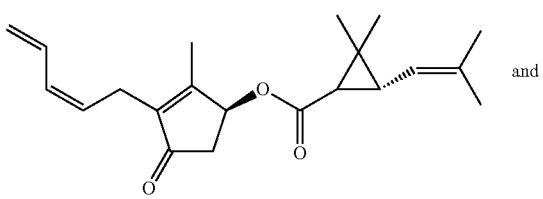

and

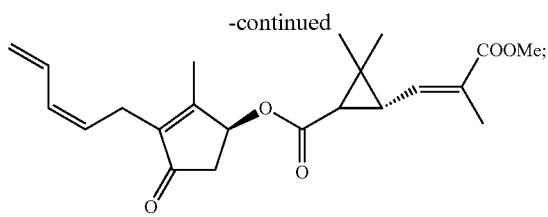

the olefin of Formula II is

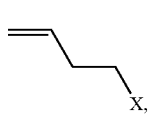

wherein X is halogen; and
the alcohol of Formula III is

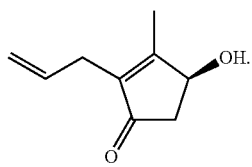

9. The method of claim 1, wherein the pyrethroid of Formula I is selected from the group consisting of

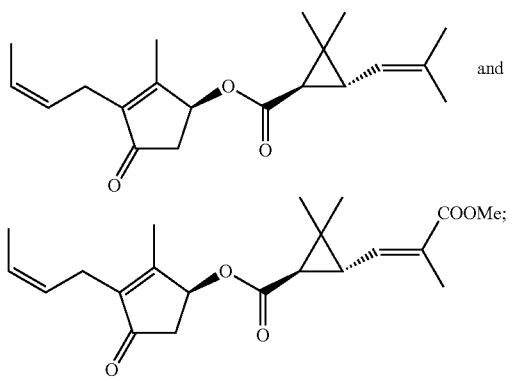

the olefin of Formula II is

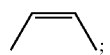

and the alcohol of Formula III is

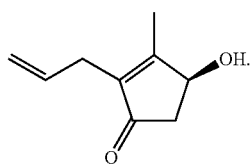

10. The method of claim 1, wherein the pyrethroid of Formula I is selected from the group consisting of

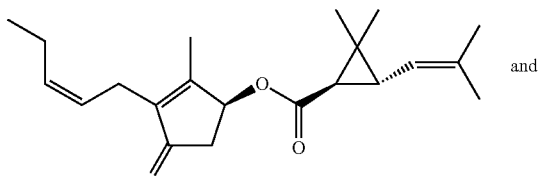

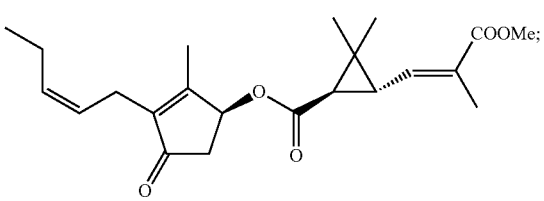

the olefin of Formula II is

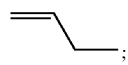

and the alcohol of Formula III is

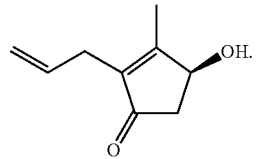

11. The method of claim 1, wherein the first reaction mixture comprises a metathesis catalyst.

12. The method of claim 11, wherein the metathesis catalyst comprises ruthenium.

13. The method of claim 12, wherein the metathesis catalyst is selected from the group consisting of:

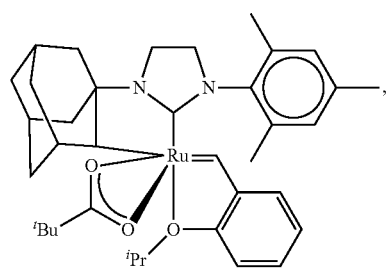

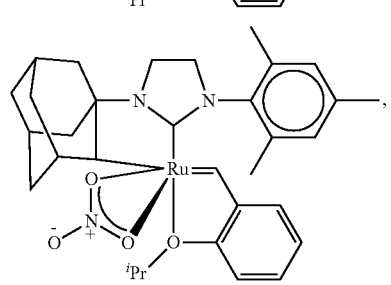

-continued

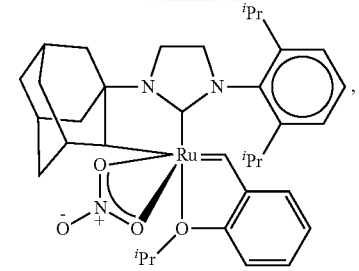

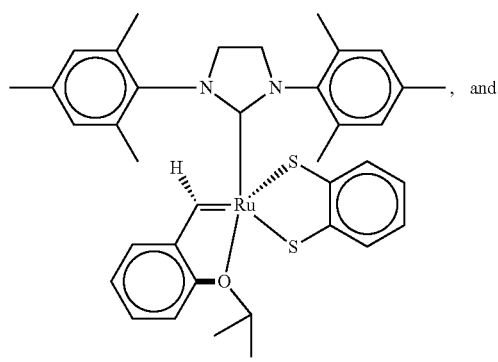

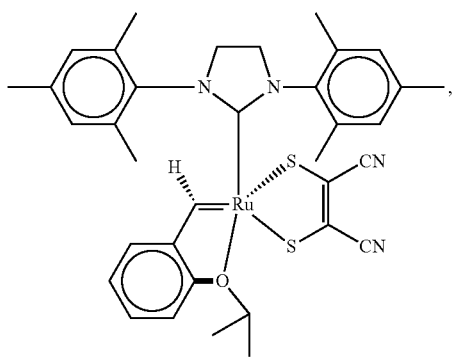

wherein $^i$Pr is isopropyl and $^t$Bu is tert-butyl.

14. The method of claim 11, wherein the first reaction mixture comprises the metathesis catalyst in an amount of from about 0.01 mol % to about 50 mol % with respect to the olefin or the alcohol.

15. An insecticidal composition comprising:

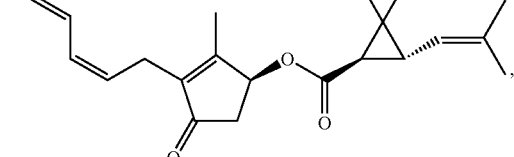

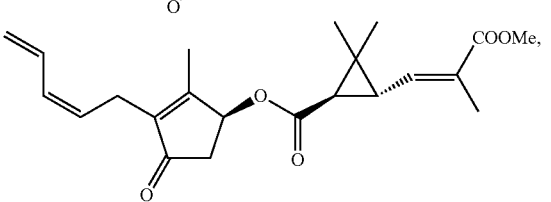

-continued

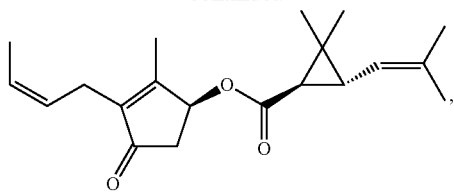

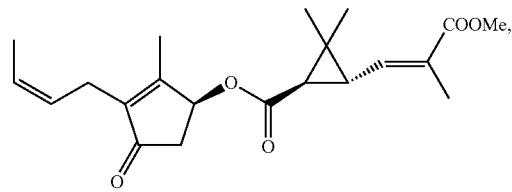

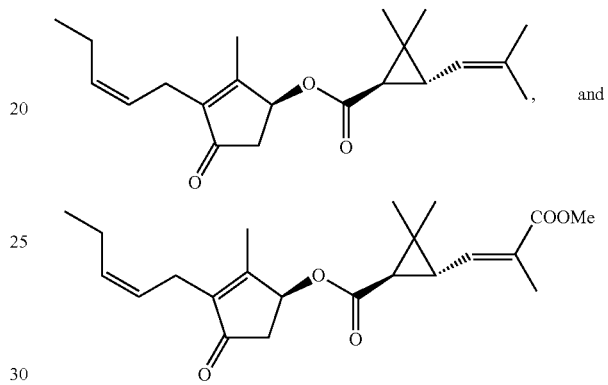

in a molar ratio of about 1:1:1:1:1:1.

16. A method for controlling insects, the method comprising applying an effective amount of an insecticidal composition comprising a pyrethroid synthesized by the method of claim 1 to a locus where control of insects is desired.

17. A method for controlling insects over multiple years, the method comprising applying an insecticidally-effective amount of an insecticidal composition comprising the pyrethroids

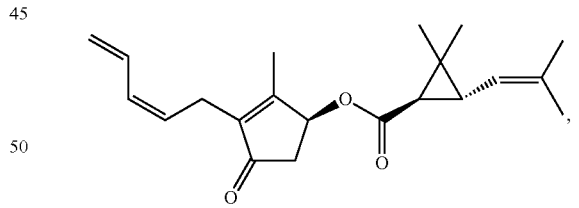

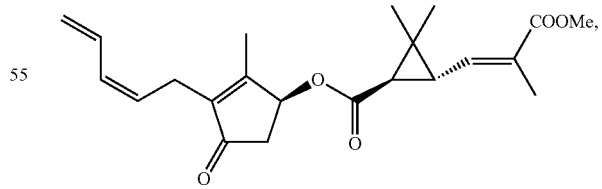

-continued
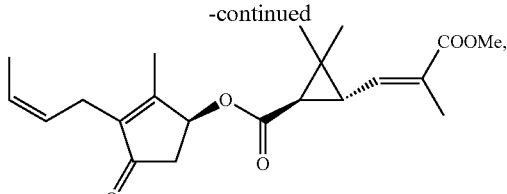
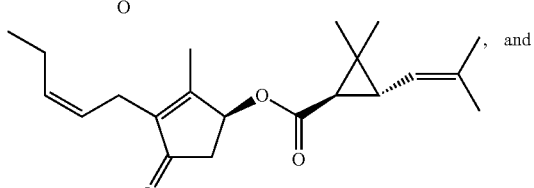
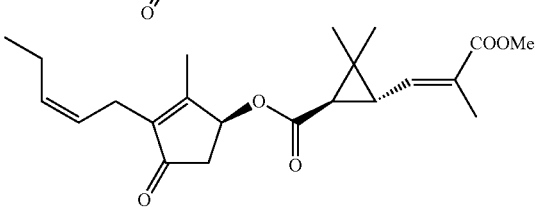
to a locus where control of insects is desired, wherein each of the pyrethroids is synthesized by the method of claim 1, and wherein the ratio of the pyrethroids varies from year to year.
* * * * *